(12) United States Patent
Meijer

(10) Patent No.: US 7,098,204 B2
(45) Date of Patent: Aug. 29, 2006

(54) HYMENIALDISINE OR DERIVATIVES THEREOF IN THE MANUFACTURE OF MEDICAMENTS

(75) Inventor: Laurent Meijer, Hakeim (FR)

(73) Assignee: C.N.R.S., Paris Cedex 16 (FR)

( * ) Notice: Subject to any disclaimer, the term of this patent is extended or adjusted under 35 U.S.C. 154(b) by 0 days.

(21) Appl. No.: 10/149,115

(22) PCT Filed: Dec. 7, 2000

(86) PCT No.: PCT/EP00/12791

§ 371 (c)(1),
(2), (4) Date: Oct. 4, 2002

(87) PCT Pub. No.: WO01/41768

PCT Pub. Date: Jun. 14, 2001

(65) Prior Publication Data

US 2003/0105075 A1    Jun. 5, 2003

(30) Foreign Application Priority Data

Dec. 8, 1999  (EP)  .................. 99403077

(51) Int. Cl.
*A61P 35/00*     (2006.01)
(52) U.S. Cl. ................................. 514/212.06
(58) Field of Classification Search ............ 514/212.06
See application file for complete search history.

(56) References Cited

U.S. PATENT DOCUMENTS

| | | | |
|---|---|---|---|
| 5,621,099 A | 4/1997 | Hirokazu et al. | |
| 5,897,203 A | 4/1999 | Rastrelli | |
| 6,884,819 B1 | 4/2005 | Suwa | |
| 6,911,475 B1 | 6/2005 | Cesaro | |
| 6,914,056 B1 | 7/2005 | Shinitzky | |
| 6,921,763 B1 | 7/2005 | Hirst | |
| 6,921,765 B1 | 7/2005 | Bykov | |
| 2005/0009876 A1 | 1/2005 | Bhagwat | |
| 2005/0137201 A1 | 6/2005 | Aronov | |

FOREIGN PATENT DOCUMENTS

| WO | WO 93 16703 | 9/1993 |
|---|---|---|
| WO | WO 96 40147 | 12/1996 |
| WO | WO 99 15157 | 4/1999 |

OTHER PUBLICATIONS

Meijer, L. et al, Chemistry & Biology, Jan. 2000, vol. 7, No. 1, pp. 51-63.
Supriyono, A. et al, Z. Naturforsch., C: Biosci, 1995, 50(9/10), pp. 669-674.
Roshak, A. et al, Journal of Pharmacology and Experimental Therapeutics, Nov. 1997, 283 (2), pp. 955-961.
Boyd, Michael R. et al, J. Nat. Prod. 1997, 60(2), pp. 180-183.
Breton, J. J. et al, Journal of Pharmacology and Experimental Therapeutics, 1997, vol. 282, No. 1, pp. 459-466.
Dimartino, M. et al, Inflammation Research, Aug. 1, 1995, vol. 44, No. Suppl. 02, pp. S123-S124.
Imburgia, C. et al, Proceedings of the American Association for Cancer Research Annual Meeting, Mar. 1999, vol. 40, pp. 406.
Pettit, George R. et al, Can. J. Chem. 1990, 68(9), pp. 1621-1624.
Kobayashi, J. et al, Experientia, 1988, 44(1), pp. 86-87.

*Primary Examiner*—Bruck Kifle
(74) *Attorney, Agent, or Firm*—Nixon & Vanderhye P.C.

(57) ABSTRACT

The invention relates to the use of hymenialdisine or derivatives thereof of formula (I) in which R1 and R2, identical or different, represent H or Br, or a pharmaceutically acceptable salt thereof, in the manufacture of a medicament for use in inhibiting acceptable salt thereof, in the manufacture of a medicament for use in inhibiting cycline dependent kineases, GSK-3β and casein kinase 1. Application for preventing and treating neurodegenerative disorders, diabetes, inflammatory pathologies and cancers.

8 Claims, 14 Drawing Sheets

Figure 1:
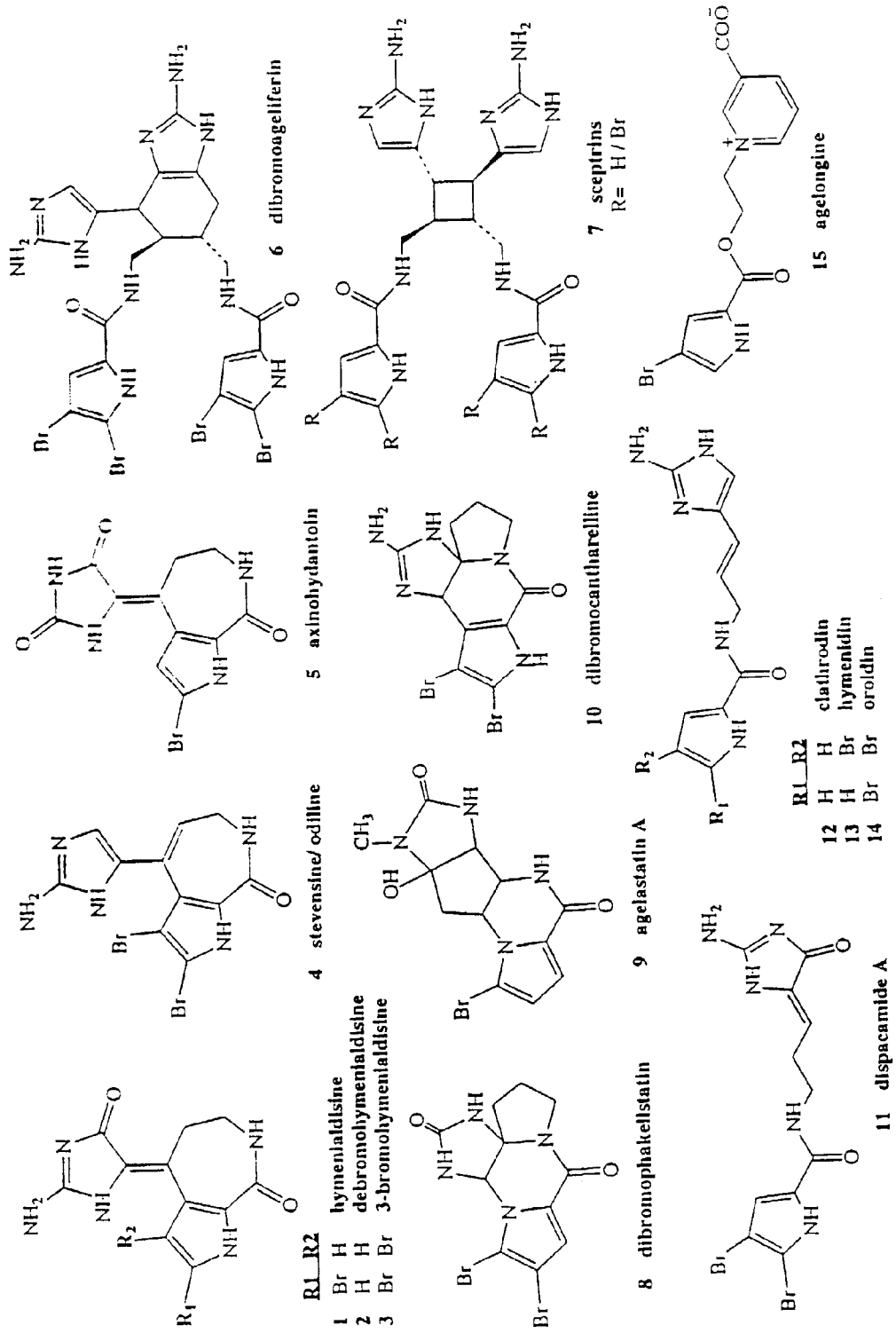

A. In vitro - GSK-3
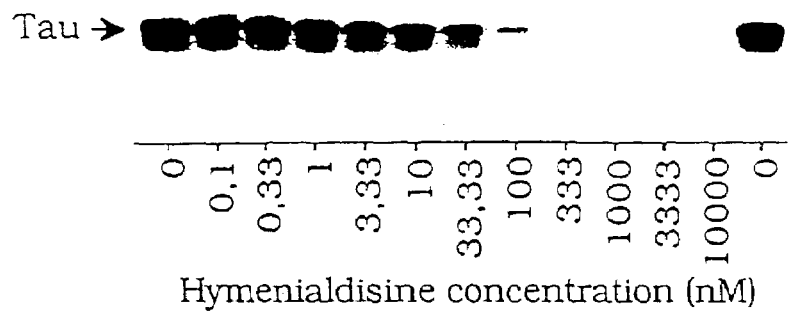
B. In vivo
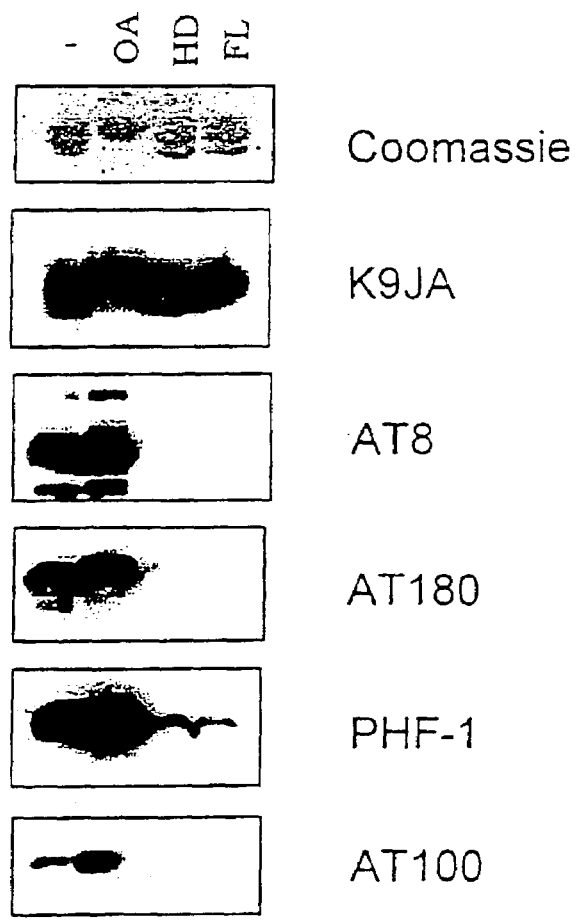
figure 5

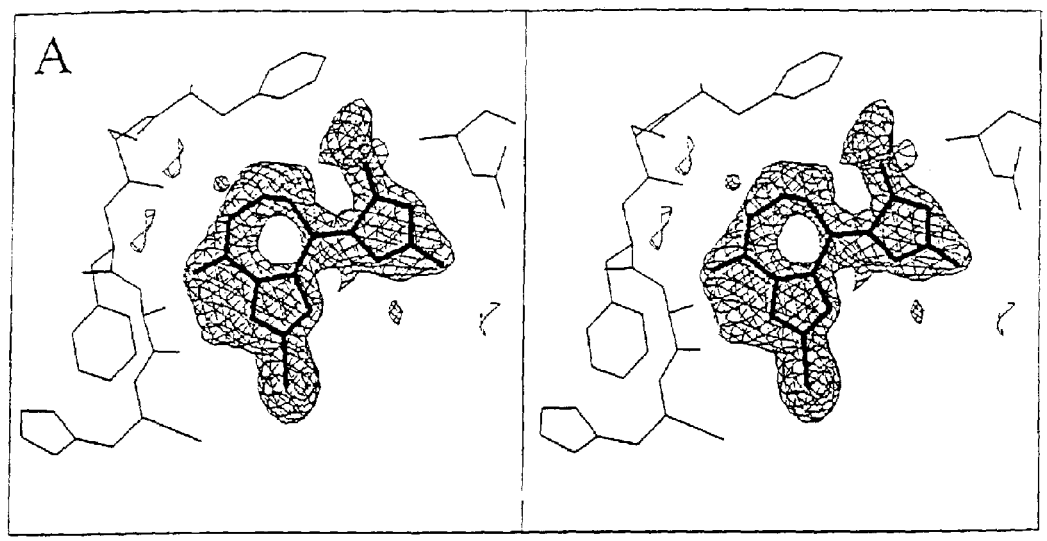
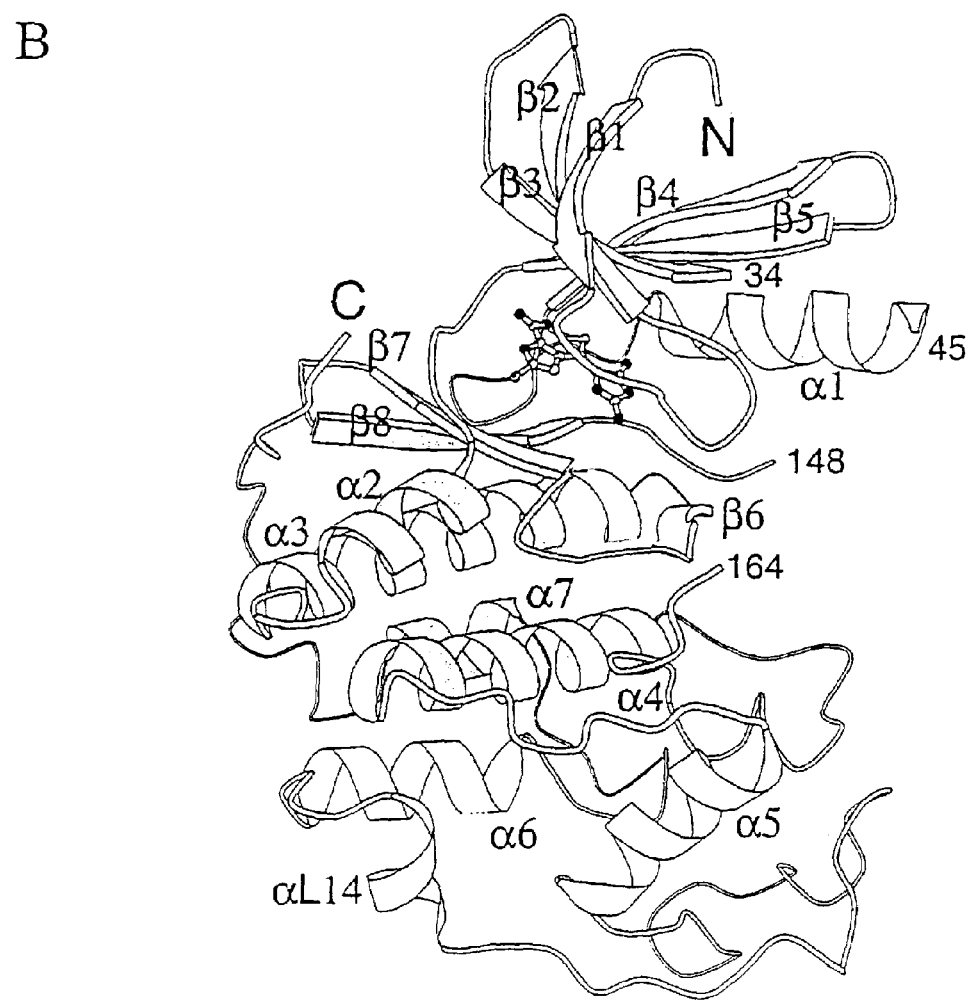
figure 7

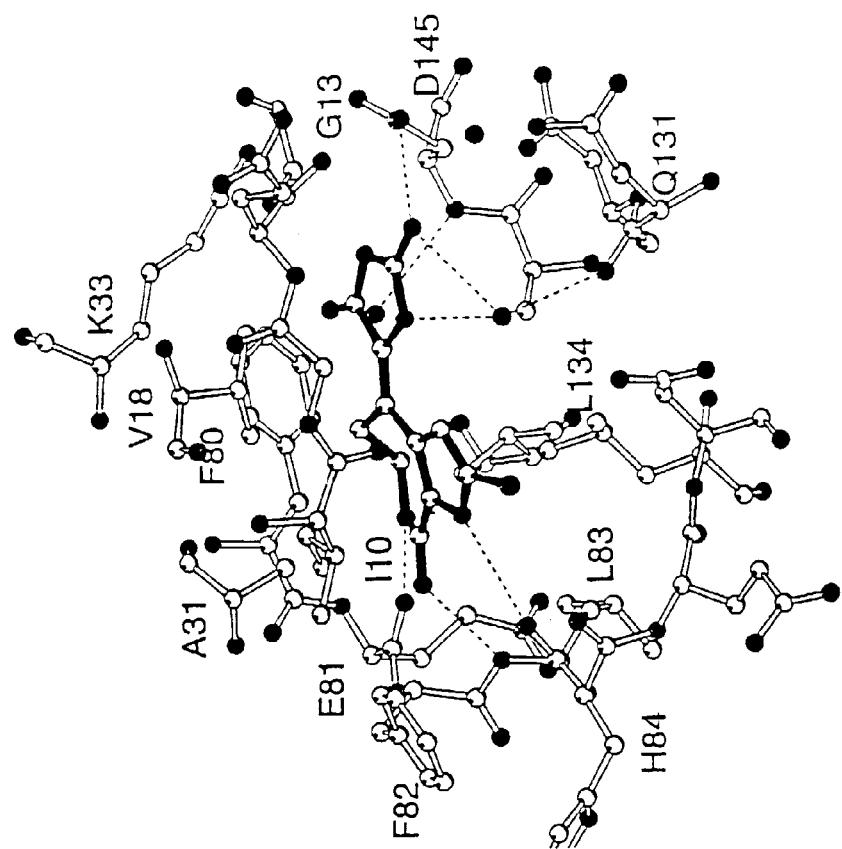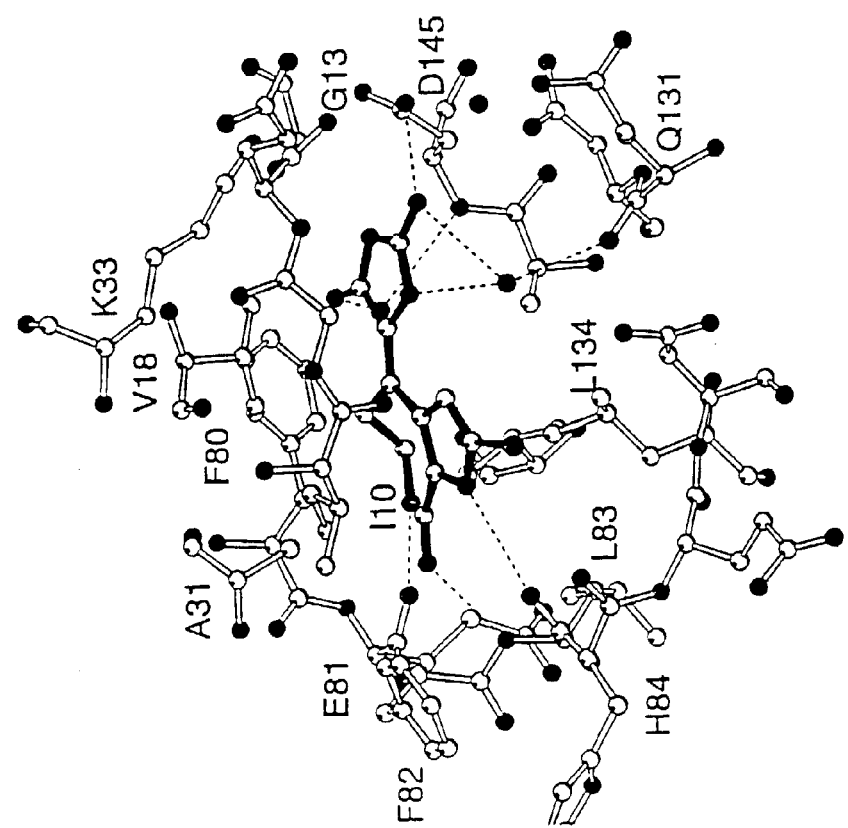
figure 8a

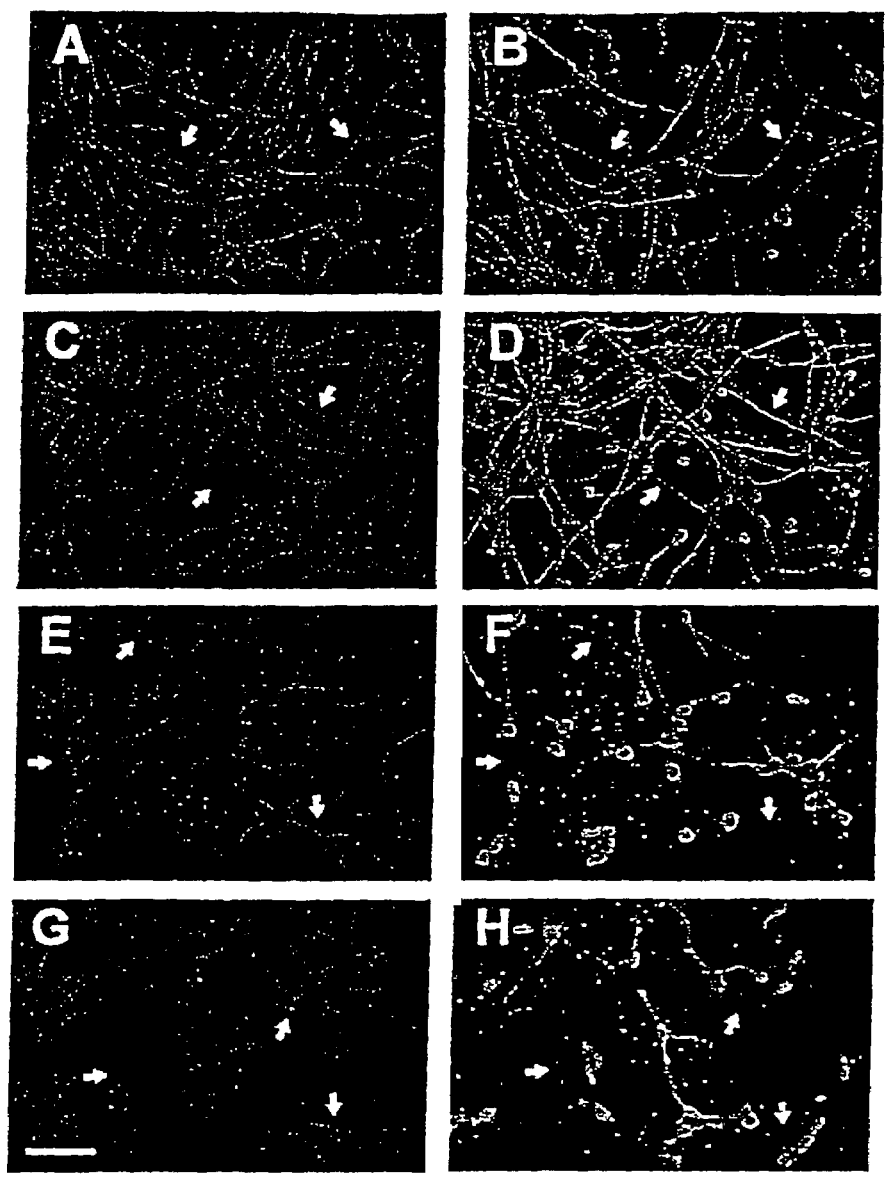
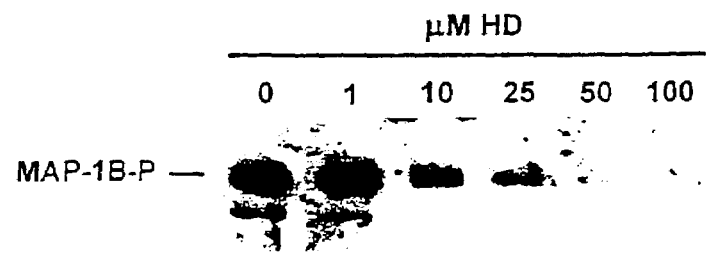
figure 10

HYMENIALDISINE OR DERIVATIVES THEREOF IN THE MANUFACTURE OF MEDICAMENTS

This application is the U.S. national phase of international application PCT/EP00/12791 filed 7 Dec. 2000, which designated the U.S. and published in English as WO 01/41768 A2.

The invention relates to the use of hymenialdisne or derivatives thereof in the manufacture of medicaments capable of blocking the cellular division or the intracellular transduction of signals.

It more particularly relates to the use of hymemnialdisine (referred to as HD hereinafter), or derivatives thereof, in the manufacture of protein kinase inhibitors.

Protein kinase are involved in cellular regulation, particularly in protein phosphorylation.

Cyclin-dependent kinase proteins (CDKs in abbreviated form) are involved in cell cycle control (CDK1, 2, 3, 4, 6 & 7), in thymocyte apoptosis (CDK2), in neuronal functions (CDK5), in transcriptional control (CDK7, 8 & 9) (reviews in [1,2,3] the list of the references being given at the end of the description). In nervous tissues CDK5/p35 phosphorylates the microtubule-associated proteins tau and MAP-1B, the Pak1 kinase and neurofilament subunits. Intensive screening has lead in a few years to the identification of a series of chemical inhibitors of CDKs, such as olomoucine, roscovitine, purvalanol, flavopiridol, indirubins, paullones. Some of these compounds display a remarkable selectivity and efficiency. Many have been co-crystallised with CDK2 and their interactions with the ATP-binding pocket of the kinase have been analysed in detail (review in [4]).

HD was also reported to inhibit protein kinase C (WO 93 16703 and WO95 31462).

It has now been found that said compound, and derivatives thereof, are potent, selective inhibitors of CDKs 1, 2 and 5 and of two other major protein kinases involved in protein phosphorylation, i-e. Glycogen synthase kinase 3-β (GSK-3β and in abbreviated form) and casein kinase 1.

The invention thus relates to the use of hymenialdisine or derivatives thereof of formula I

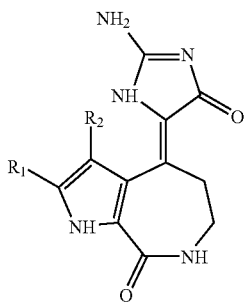

in which $R^1$ and $R^2$, identical or different, represent H or BR, or a pharmaceutically acceptable salt thereof, in the manufacture of a medicament for use in onhibiting cyclin-dependent kinases, GSK-3β and casein kinase 1.

The term "derivatives", as used in the specification, comprises the above-defined salts.

In a preferred use, the compound is 4-(2-amino-4-oxo-2-imidazolin-5-ylidene)-4,5,6,7-tetrahydropyrrolo (2,3-c) azepine-8-one, or a pharmaceutically acceptable salt thereof.

In another preferred use, the compound is 4-(2-amino-4-oxo-2-imidazolin-5-ylidene)-2-bromo-4,5,6,7-tetrahydropyrrolo (2,3-c) azepine-8-one, or a pharmaceutically acceptable salt thereof.

As observed with other CDKs inhibitors, HD and derivatives thereof act by competition with ATP. They interact with the ATP-binding pocket through three hydrogen bonds with the Glu-81 and Leu-83 residues of CDK2.

Hymenialdisine derivatives capable of forming hydrogen bonds with the Glu-81 and Leu-83 residues of CDK2 are also part of the invention.

As above-mentioned, said compounds strongly inhibit CDK1, CDK2, CDK5, GSK-3β and casein kinase 1.

In vivo experiments in several models have shown that HD and its derivatives inhibit CDK5/p35 as demonstrated by the lack of phosphorylation/down-regulation of Pak1 kinase in E18 rat cortical neurones.

They also inhibit GSK-3β in vivo as shown by the inhibition of MAP-1B phosphorylation on a GSK-3β-specific site. They also block the in vivo phosphorylation of the microtubule-binding protein tau at sites which are hyperphosphorylated by GSK-3β and CDK5/p35 in Alzheimer's disease.

By acting on said kinases, which represent the major kinases involved in the hyperphosphorylation of substrates involved in neurodegenerative diseases, said compounds are of great interest for manufacturing medicaments for treating and preventing corresponding conditions.

Accordingly, the invention relates to the use of HD and its derivatives for manufacturing medicaments useful for treating neurodegenerative diseases.

Said medicaments can be used for treating or preventing Alzheimer's disease, or other neuronal disorders, such as Parkinson's disease, multiple system atrophy. They are also useful for treating dogs with hereditary canine spinal muscular atrophy.

The invention also relates to the use of HD and its derivatives for manufacturing medicaments efficacious in the prevention and the treatment of diabetes. As said compounds are GSK-3β inhibitors, they constitute insulinomimetics of great interest in that respect.

The anti-inflammatory properties of HD and its derivatives are also used for manufacturing medicaments useful for treating and preventing such conditions.

By acting on said kinases, and particularly on CDKs, said compounds also have antiproliferative effects resulting in antitumoral properties of great interest. The invention thus also relates to the use of HD and its derivatives for manufacturing medicaments for preventing and treating cancers.

The compounds of formula I can be isolated from marine invertebrates [5].

HD has been found in species of marine sponges belonging to the Agelasidae, Axinellidae and Halichondriidae families. These animals contain a variety of substances which are clearly metabolically related to HD (FIG. 1).

Pharmaceutically acceptable acid addition salts of compounds of formula I are formed with organic or inorganic acids according to usual methods.

Suitable acids comprise acetic, ascorbic, maleic, phosphoric, salicylic and tartric acids.

The medicaments comprise an effective amount of the above-mentioned compounds in association with a pharmacologically acceptable carrier.

Said carrier may be solid or liquid depending on the administration form.

The medicaments can be administered in various forms: parenterally, rectally, topically, transdermally or orally. They are more particularly administered by the oral or injectable route.

For administration by the oral route, lozenges, compressed tablets, pills, tablets, capsules, drops, syrups, suspensions or emulsions, may be used. These compositions advantageoulsy comprise 100 to 1000 mg of active prinicpe per dose unit, preferably 300 to 600 mg.

Other forms of administration include injectable solutions for the intravenous, subcutaneous or intramuscular route, formulated from sterile or sterilizable solutions. They can also be suspensions or emulsions.

These injectable forms comprise 100 to 1000 mg of a compound of formula I, or a pharmaceutically acceptable salt thereof, preferably 300 to 600 mg, per dose unit.

By way of indication, the dosage which can be used in a patient in need thereof corresponds to the following doses: for example, 100 to 1000 mg/day are thus administered to the patient 1 to 4 times per day for the treatment of neurodegenerative disorders.

The invention also relates to biological reagents, the active principles of which consist of the compounds of formula I as above-defined.

These reagents can be use as references or standards in studies of cell division and phosphorylation mechanisms.

Figure 2:
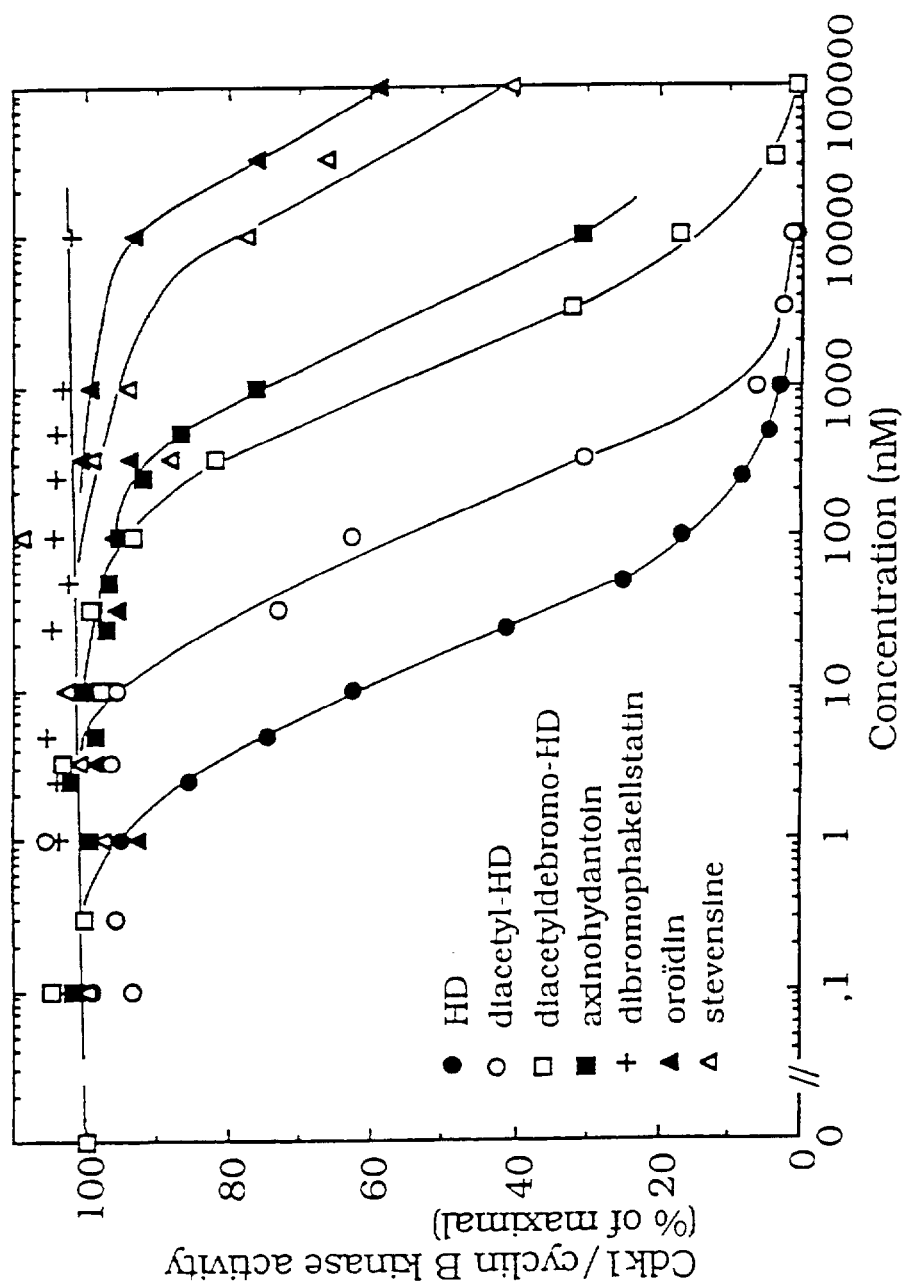
Figure 3:
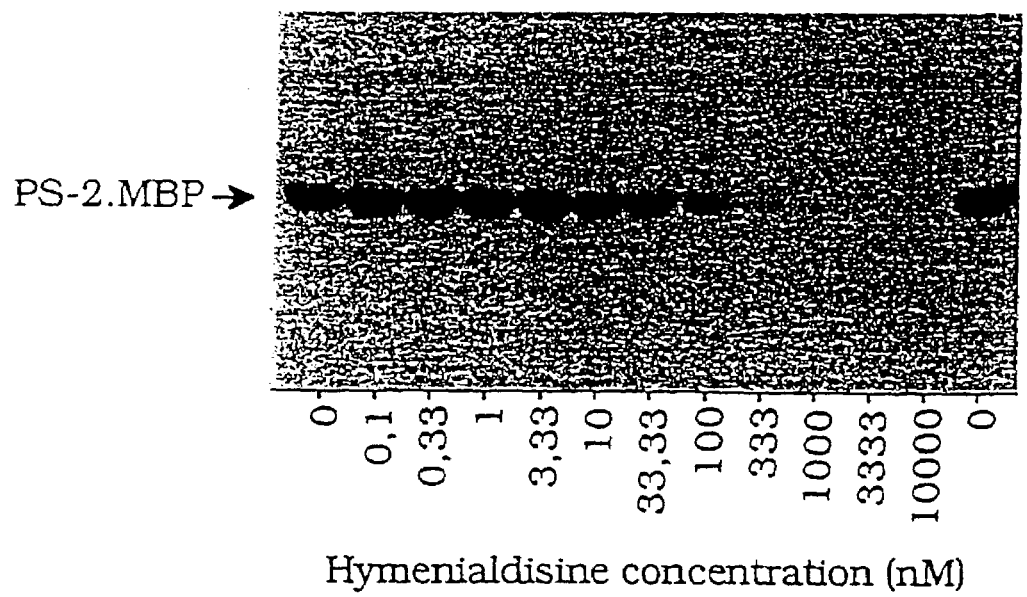
Figure 4:
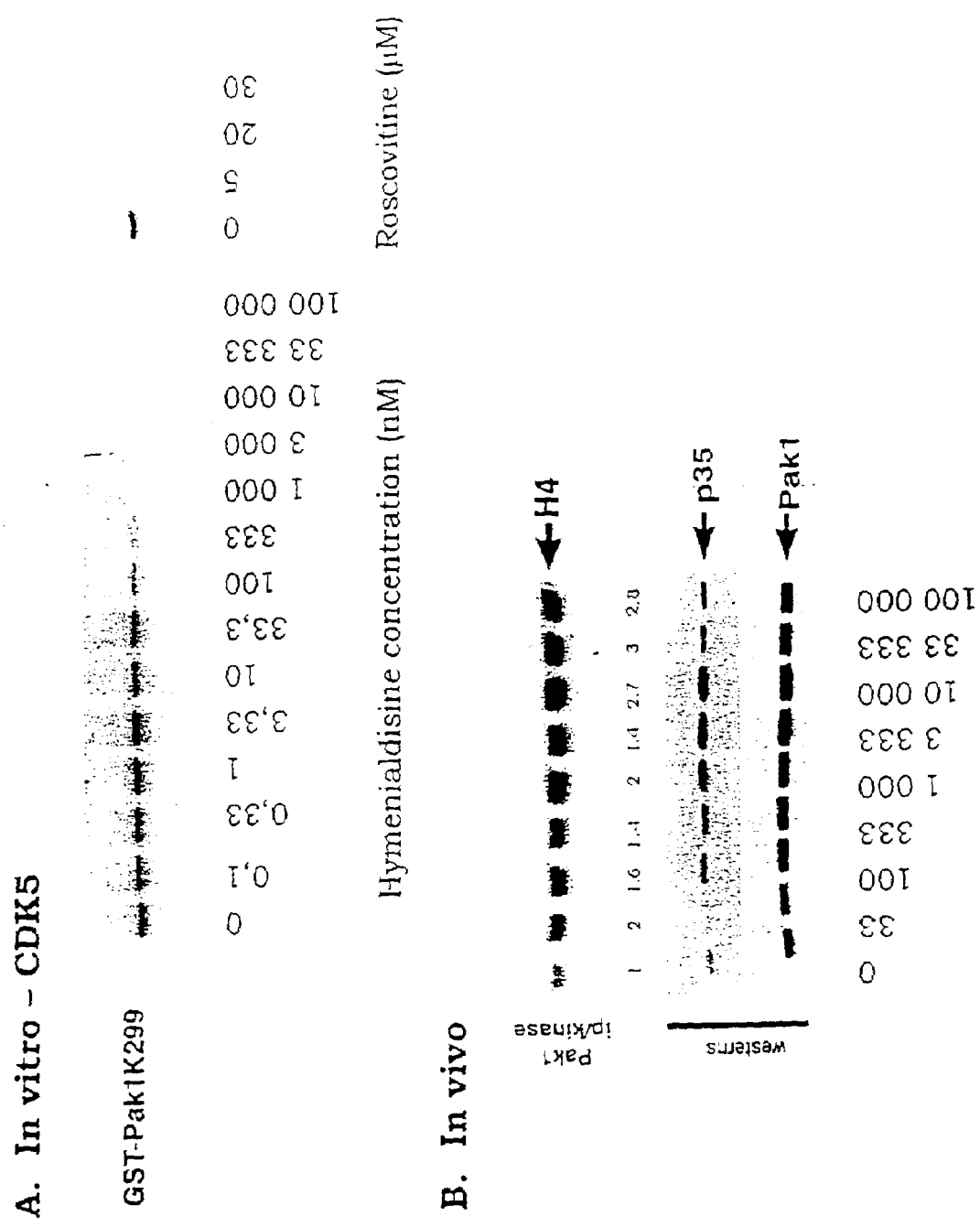
Figure 6:
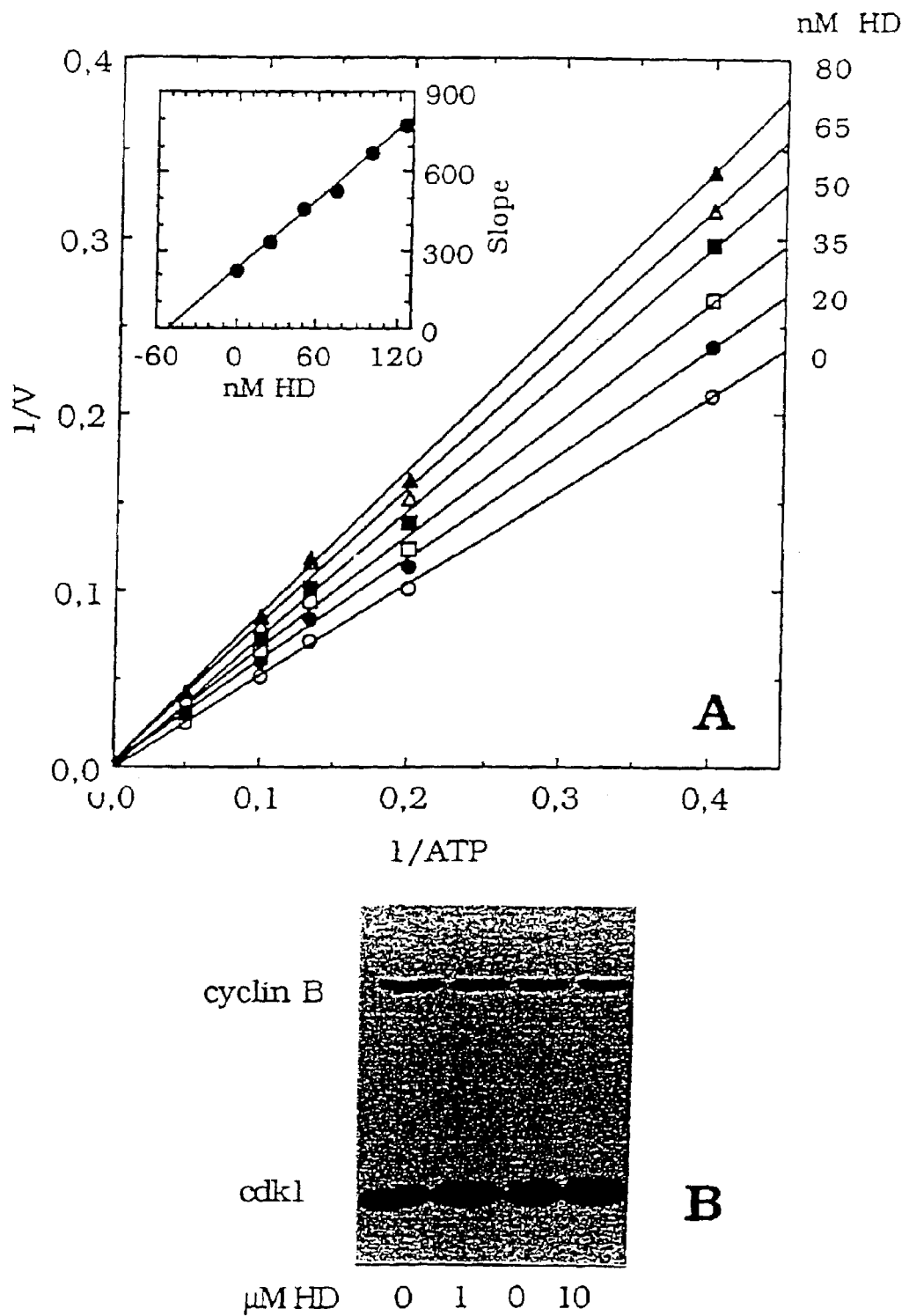
Figure 8B:
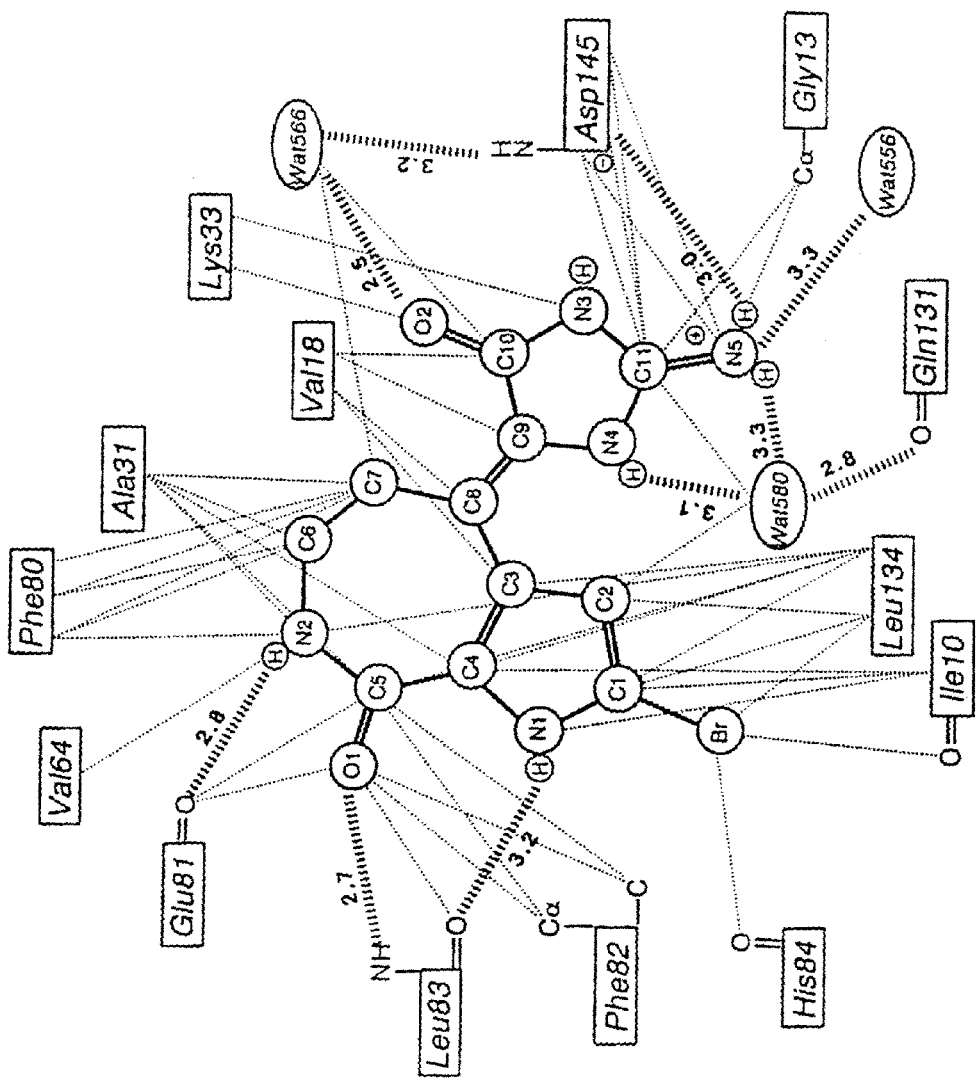
Figure 9:
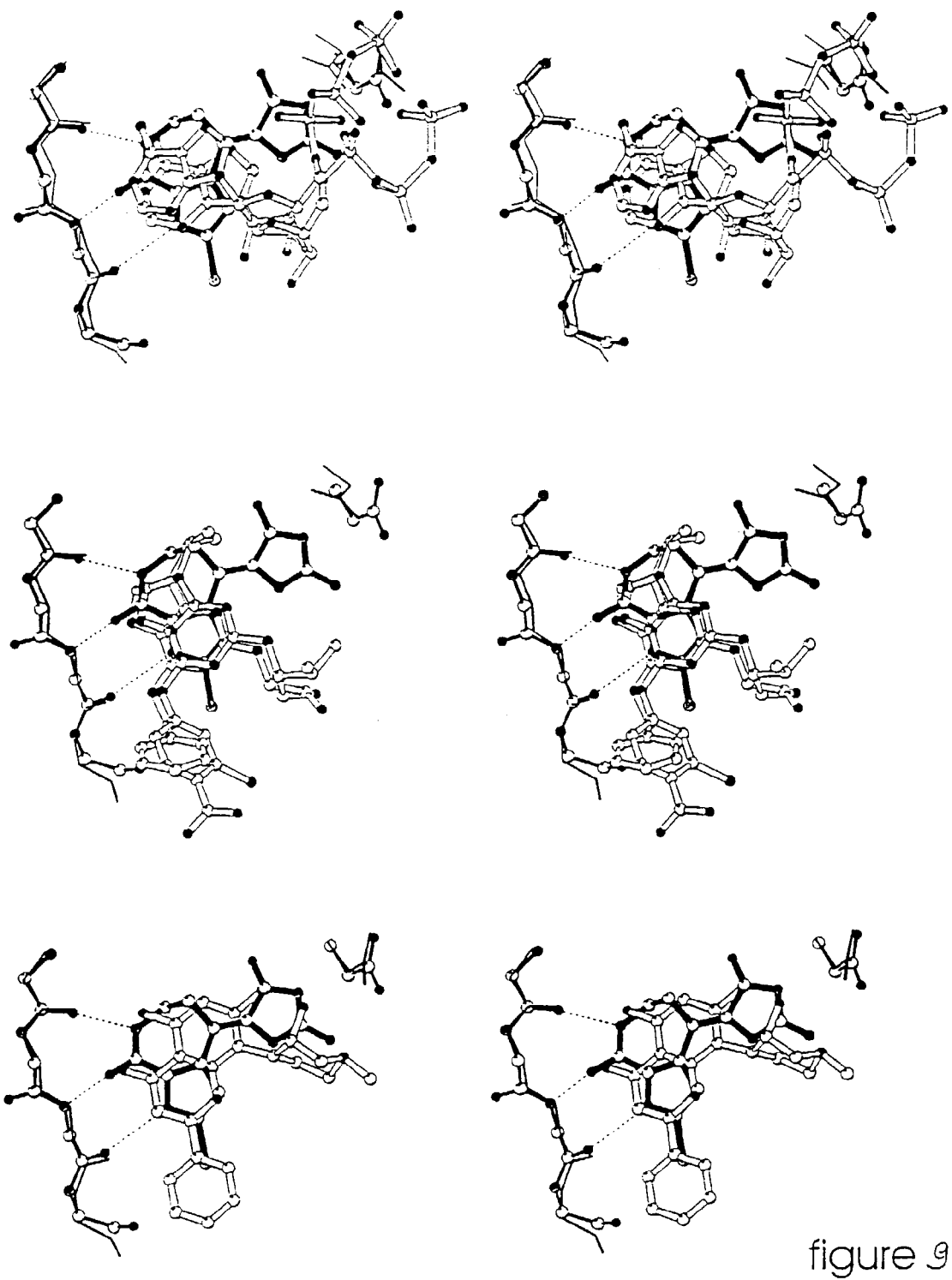
Figure 14:
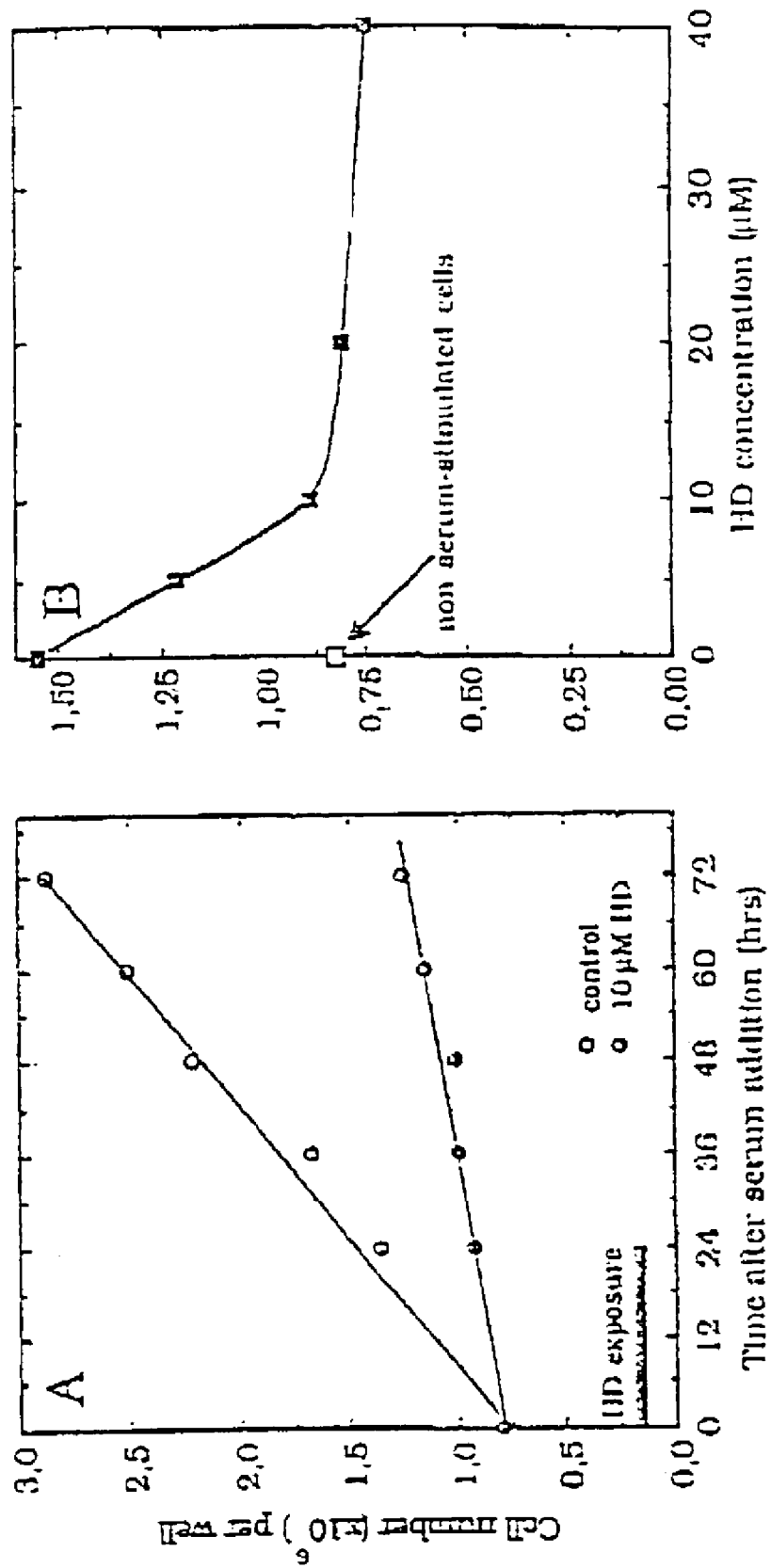
Figure 12:
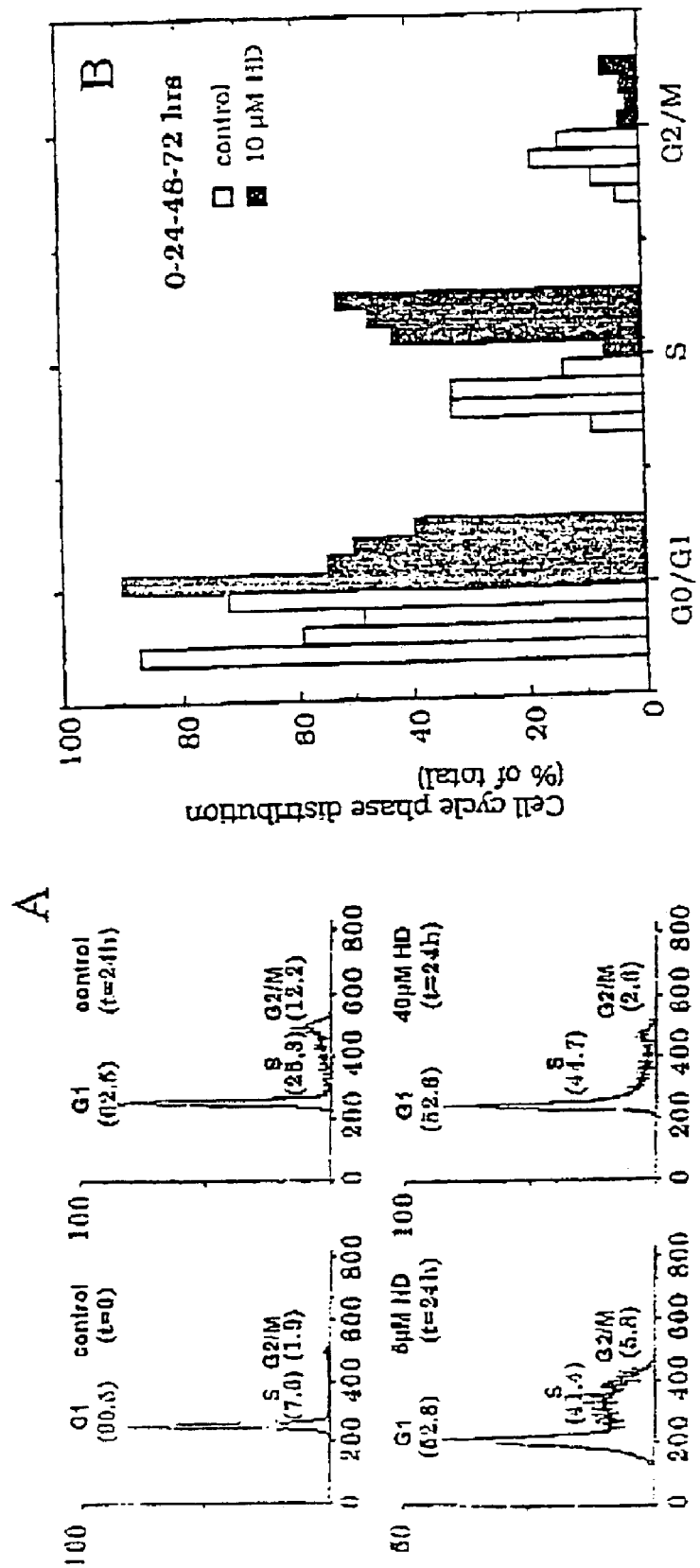
Figure 13:
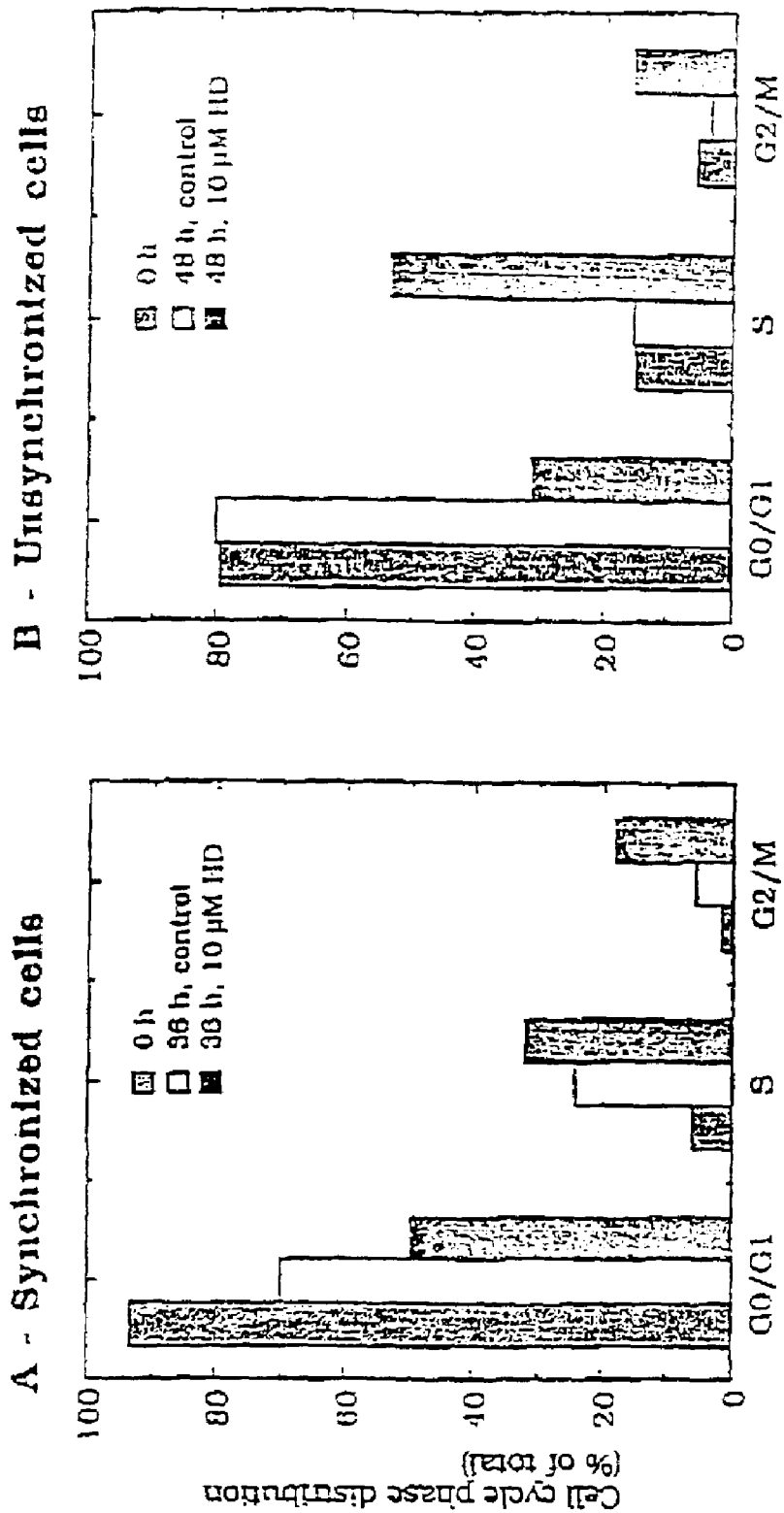

Other characteristics and advantages of the invention are described in the examples which follow with reference to FIGS. 1 to 13 in which FIG. 1 represents the structure of hymenialdisine and related metabolites isolated from marine sponges, FIG. 2, the CDK1/cyclin B kinase activity in the presence of increasing concentrations of HD and analogues, FIG. 3, the autoradiography obtained with a presenilin-MBP fusion protein phosphorylated in vitro with casein kinase 1 in the presence of increasing HD concentrations and resolved by SDS-PAGE, FIG. 4A represents the inhibition by HD of Pak1 phosphorylation by CDK5/p35 in vitro and in vivo (FIG. 4A shows the level of H4 phosphorylation following SDS-PAGE of the substrate, and FIG. 4B, the Western blots showing amounts of Pak1 and p35), FIG. 5A, the autoradiography of r-htau phosphorylated in vitro with GSK-3β in the presence of increasing HD concentrations and resolved by SDS-PAGE, and FIG. 5B, the inmmunoblot results obtained by reacting, with various antibodies, preparations of htau23, exposed, or non exposed, to CDKs inhibitors in vivo, FIG. 6A, kinetic data from assays of CDK/1 cyclin B protein kinase activity at different concentrations of HD, and FIG. 6B the results obtained when exposing inmmobilised CDK1/cyclin B to HD and Western blotting with anti-cyclin B and anti-PSTAIRE antibodies, FIG. 7, a stereo view of the electron density map for HD in complex with CDK2, FIG. 8A, a stereo diagram showing the refined structure of HD in the ATP binding pocket of CDK2 and FIG. 8B, the schematic illustration of the interactions between CDK2 and HD, FIG. 9, stereo views showing the comparison of HD-CDK2 binding with those of other CDK2 ligands, FIG. 10, the results obtained by double immunofluorescence staining for GAP-3 and MAP-1B-P depending on HD concentrations (A–H), and Western blot results with cell lysates in response to increasing doses of HD, FIG. 11, the effect of HD on HT 29-18-C1 cells growth, FIGS. 12 and 13, the cellular effects of HD with the arrest in S phase (FIG. 12) and at the G2/Mtransition (FIG. 13)

I/MATERIAL AND METHODS

Chemicals and Reagents

Sodium ortho-vanadate, EGTA, EDTA, RNAse A, Mops, β-glycerophosphate, phenylphosphate, sodium fluoride, glutathione-agarose, dithiothreitol (DTT), bovine serum albumin (BSA), nitrophenylphosphate, leupeptin, aprotinin, microcystin pepstatin, soybean trypsin inhibitor, benzamidine, histone HI (type III-S), myelin basic protein, casein were obtained from Sigma Chemicals, [γ-$^{32}$P]-ATP (PB 168) from Amersham.

The GS1 peptide (YRRAAVPPSPSLSRHSSPHQS-pEDEEE) was obtained by synthesis.

Hymenialdisine was isolated as previously described [6,7] and dissolved as a 10–50 mM stock solution in dimethyl-sulfoxide (DMSO). It was diluted to 5–10 mM in Me$_2$SO just prior to using in aqueous buffers. Final DMSO concentration in the reaction mixture was below 1% (v/v).

Axinohydantoin [7], hymenialdisine-platinum complex, diacetylhymenialdisine, diacetyl-debromohymenialdisine, dibromophakellstatin [6], agelastatin A [8], dibromoageliferin, clathrodin, hymenidin, dibromocantharelline [9] were prepared in the laboratory. Agelongine [10], dispacamide B [11], sceptrin [12], oroydin [13] and stevensine (odiline) [14,9] were purified from *Agelas* sp.

GST-Retinoblastoma protein was expressed in bacteria and purified on glutathione-Sepharose beads as previously described [15]. p9$^{CKShs1}$-Sepharose beads were prepared as previously described [16].

Buffers

Homogenization Buffer: 60 mM β-glycerophosphate, 15 mM p-nitrophenyl-phosphate, 25 mM Mops (pH 7.2), 15 mM EGTA, 15 mM MgCl$_2$, 1 mM DTT, 1 mM sodium vanadate, 1 mM NaF, 1 mM phenylphosphate, 10 µg leupeptin/ml, 10 µg aprotinin/ml, 10 µg soybean trypsin inhibitor/ml and 100 µM benzamidine.

Buffer A: 10 mM MgCl$_2$, 1 mM EGTA, 1 mM DTT, 25 mM Tris-HCl pH 7.5, 50 µg heparin/ml.

Buffer C: homogenization buffer but 5 mM EGTA, no NaF and no protease inhibitors.

Hypotonic Lysis Buffer (HLB): 50 mM Tris-HCl pH 7.4, 120 mM NaCl, 10% glycerol, 1% Nonidet-P40, 5 mM DTT, 1 mM EGTA, 20 mM NaF, 1 mM orthovanadate, 5 µM microcystin, 100 µg/ml each of leupeptin, aprotinin and pepstatin.

Tris-Buffered Saline-Tween-20 (TBST): 50 mM Tris pH 7.4, 150 mM NaCl, 0.1% Tween-20.

STM buffer: 10 mM Tris-HCl pH 8.0, 0.25 M sucrose, 10 mM MgCl$_2$, 1 mM DTT, protease and phosphatase inhibitors [17].

Kinase Preparations and Assays

Kinases activities were assayed in Buffer A or C (unless otherwise stated), at 30° C., at a final ATP concentration of 15 µM. Blank values were subtracted and activities calculated as pmoles of phosphate incorporated for a 10 min. incubation (usually expressed in % of the maximal activity, i.e. without inhibitors). Controls were performed with appropriate dilutions of Me$_2$SO. In some cases phosphorylation of the substrate was assessed by autoradiography after SDS-PAGE. IC$_{50}$ values were estimated from the dose-response curves.

CDK1/cyclin B was extracted in homogenisation buffer from M phase starfish (*Marthasterias glacialis*) oocytes and purified by affinity chromatography on p9$^{CKShs1}$-Sepharose beads, from which it was eluted by free p9$^{CKShs1}$ as described [15, 16]. The kinase activity was assayed in buffer C, with 1 mg histone H1/ml, in the presence of 15 μM [γ-$^{32}$P] ATP (3,000 Ci/mmol; 1 mCi/ml) in a final volume of 30 μl. After 10 min. incubation at 30° C., 25 μl aliquots of supernatant were spotted onto 2.5×3 cm pieces of Whatman P81 phosphocellulose paper, and, 20 sec. later, the filters were washed five times (for at least 5 min. each time) in a solution of 10 ml phosphoric acid/liter of water. The wet filters were counted in the presence of 1 ml ACS (Amersham) scintillation fluid.

GSK-3β was either purified from rabbit muscle or expressed in and purified from insect Sf9 cells [18]. It was assayed, following a 1/100 dilution in 1 mg BSA/ml 10 mM DTT, with 5 μl 40 μM GS-1 peptide as a substrate, in buffer A, in the presence of 15 μM [γ-$^{32}$P] ATP (3,000 Ci/mmol; 1 mCi/ml) in a final volume of 30 μl. After 30 min. incubation at 30° C., 25 μl aliquots of supernatant were spotted onto P81 phosphocellulose papers and treated as above described.

CDK5/p25 was reconstituted by mixing equal amounts of recombinant CDK5 and p25 expressed in *E. coli* as GST (Glutathione-S-transferase) fusion proteins and purified by affinity chromatography on glutathione-agarose (p25 is a truncated version of the CDK5 activator). Its activity was assayed in buffer C as described for CDK1/cyclin B.

CDK2/cyclin A, CDK2/cyclin E, CDK3/cyclin E, CDK4/cyclin D1, CDK6/cyclin D2, His-tagged erk1 and erk2, protein kinase C isoforms, the catalytic subunit of cAMP-dependent protein kinase, cGMP-dependent protein kinase, Myosin light chain kinase, casein kinases 1 & 2, ASK-γ (a plant homologue of GSK-3), insulin receptor tyrosine kinase domain (CIRK-41), c-raf, MAPKK, c-jun N terminal kinase (obtained from Promega), c-src kinase and v-abl kinase were assayed as described [15].

Electrophoresis and Western Blotting

Proteins bound to p9$^{CKShs1}$-Sepharose beads (starfish CDK1/cyclin B) were denatured with 2× Laemmli sample buffer. Samples were run on 10% SDS-polyacrylamide gels. Proteins were transferred from the gel to a 0.1 μm nitrocellulose sheet in a milliblot-SDE system (Millipore) for 30 min. at 2.5 mA/cm$^2$ in transfer buffer. Subsequently, the filter was blocked with 5% low fat milk in TBST for 1 hour. The filter was then washed with TBST and incubated for 1 hour with the first antibodies (anti-PSTAIRE, 1:2000; anti-cyclin B, 1:1000). After 4 washes (1×20 min., 3×5 min.) with TBST, the nitrocellulose sheet was treated for 1 hour with horseradish peroxidase-coupled secondary antibodies diluted in TBST (1:1000). The filter was then washed 5 times (1×20 min., 4×5 min.) with TBST and analysed by enhanced chemioluminescence with ECL detection reagents and hyperfilm MP.

Preparation of CDK2/HD Crystals.

Human CDK2 was purified and crystallized as previously described [19]. A procedure involving chemical cross-linking was employed to prevent crystals from cracking. Crystals were first soaked in a solution containing 0.5 mM ATP, 1 mM MgCl$_2$ for 2 hours, then cross-linked with 0.1% glutaraldehyde, for 1 hour at 4° C. After extensive washing the crystals were transferred to an inhibitor solution in 0.2 M HEPES, 5% ethylene glycol and 1% DMSO. This protocol allowed crystals to be soaked at inhibitor concentrations up to 0.5 mM, for several days, without showing any damage.

Determination of the CDK2/HD Crystal Structure.

X-ray diffraction data to 2.1 Å resolution were collected on a single CDK2/HD crystal using an R-Axis II image plate detection system, mounted on a Rigaku rotation-anode generator. Data were collected at 120 K to prevent radiation damage of the crystal. Just prior to freezing, the crystal was transferred to a cryo-protecting solution containing 25% ethylene glycol. Flash freezing was achieved in a dry nitrogen stream using a Molecular Structure Corporation cryodevice. Freezing altered slightly the unit cell dimensions and increased the mosaic spread from 0.2 to 0.6°. The cross-linking by itself did not alter the diffraction characteristics significantly. The intensity data were processed with the DENZO and SCALEPACK programs [20]. The program TRUNCATE, as implemented in the CCP4 suite [21], was used to obtain the final set of structure factor amplitudes. A summary of the data processing statistics is presented in Table 3. Refinement of the CDK2/HD complex was started from the coordinates of the highly refined CDK2/ATP model. All refinement steps were carried out using the program X-PLOR [22]. Molecular replacement followed by rigid body refinement was necessary to successfully reorient and reposition the CDK2 molecule in the unit cell of the frozen crystal. The model was then further refined using several rounds of conjugated-gradient energy minimization. After this stage clear electron density, calculated from $2F_o - F_c$ and $F_o - F_c$ Fourier maps, indicated the binding mode of the hymenialdisine inhibitor. Initial coordinates and geometric restraint terms for hymenialdisine were taken from the small molecule structure of Mattia et al. [23] Refinement of the CDK2/HD model was then pursued with several rounds of both X-ray restrained energy minimization and molecular dynamics, alternated with model building. Towards the end of the refinement several water molecules and a few molecules of ethylene glycol were added to the model. The stereochemistry of the CDK2/HD model was verified using the software package PROCHECK [24].

In Vitro Phosphorylation of Presenilin-2

The large hydrophilic loop of presenilin-2 between transmembrane domains 6 and 7 was expressed in *E. coli* as a presseilin-2 loop—maltose-binding protein (MBP) fusion protein [25]. Following affinity chromatography purification presenilin-2-MBP was used as a substrate for CK1. After 30 min incubation in the presence of various HD concentrations, the kinase reaction was stopped by addition of Laemmli sample buffer. MBP-presenilin-2 was resolved by SDS-PAGE and its phosphorylation level visualised by autoradiography.

In Vitro and In Vivo Pak1 Phosphorylation by CDK5/p35

In Vitro Pak1 Phosphorylation

CDK5/p35 was immunoprecipitaed from P02 rat cortices using the C-terminal Santa Cruz antibody (400 μg total protein per kinase assay). The immunoprecipitate was split into equal aliquots and the kinase assays performed using GST-Pak1 K299 as a substrate. Roscovitine, HD or DMSO were added to the beads just prior to the kinase assay, as described [17]. Phosphorylation was monitored by autoradiography.

In Vivo Pak1 Phosphorylation

HD was added onto cultured neurones obtained from E18 rat embryo cortices when the cultures were 4 days old. As a control DMSO was used to the maximal volume of drug used (7.5 μl). The drug was left on the cells for 1 hour. The cells were then lysed on ice in STM buffer and the membrane fraction isolated with STM containing 0.5% NP-40 [17].

Pak1 immunoprecipitations were carried out using a specific polyclonal antibody, followed by kinase assays using histone H4 as a a substrate. The amount of H4 phosphorylation, reflecting the level of Pak1 activity, was determined by measuring the intensity of the bands on autoradiography film and quantitating with NIH imaging program.

As loading controls Pak1 and p35 western blots were made. The latter protein increases in amount with the level of CDK5/p35 kinase inhibition.

In Vivo MAP-1B Phosphorylation by GSK-3 and Immunochemistry

Cerebellar granule cells were isolated from newborn mice and purified according to the method of Hatten [26] using Percoll gradients. Cells were plated onto dishes coated with poly-D-lysine (100 µg/ml) and laminin (50 µg/ml) and grown in serum-free medium for 1 day, the cultures were then treated with HD (1–100 µM) for 20 h. Cultures were fixed with 4% formaldehyde in PBS and stored in PBS at 4° C. Cells were permeabilised with 100% methanol and incubated with primary antibodies against GAP-43 and MAP-1B-P (SMI-31, Affiniti) overnight at 4° C. FITC and Texas Red conjugated secondary antibodies were used (Vector). For western blot analysis, cells were lysed in sample buffer and analysed by 8% SDS-PAGE. Proteins were transferred to nitrocellulose membranes and incubated with an antibody to MAP-1B-P (SMI-31) diluted in block solution (0.1% Tween-20, 3% dried skimmed milk in TBS) for 2 h at room temperature. HRP-conjugated secondary antibodies (Amersham) were used and proteins were visualised using the ECL system (Pierce). Blots were scanned using a flat bed scanner (UMAX Astra 1200S).

In Vitro and In Vivo Tau Phosphorylation

Cells and viruses. Sf9 cells (InVitrogen, San Diego, Calif.) were grown at 27° C. in monolayer culture Grace's medium (Gibco BRL, Gaithersburg, Md.) supplemented with 10% fetal bovine serum and 50 µg gentamycin/ml and 2.5 µg amphotericin/ml. BaculoGold was obtained from PharMingen (San Diego, Calif.), pVL1392 from In Vitrogen.

Tau transfection. The gene for htau23, the shortest human tau isoform [27] was excised from the bacterial expression vector pNG2 [28] with XbaI and BamHI, and inserted into the baculovirus transfer vector pVL1392 cut with the same restriction endonucleases. The BaculoGold system was used to construct the tau baculovirus containing vector. The BaculoGold DNA is a modified type of baculovirus containing a lethal deletion. Cotransfection of the BaculoGold DNA with a complementing baculovirus transfer vector rescued the lethal deletion of this virus DNA and reconstituted viable virus particles carrying the htau23 coding sequence. Plasmid DNA used for transfections was purified using QIAGEN cartridges (Hilden, Germany). Sf9 cells grown in monolayers ($2 \times 10^6$ cells in a 60 mm cell culture dish) were cotransfected with baculovirus DNA (0.5 µg BaculoGold DNA) and with vector derivatives of pVL1392 (2 µg) using a calcium phosphate coprecipitation method. The presence of recombinant protein was examined in the infected cells 5 days post infection by SDS-PAGE and Western blotting.

Tau Phosphorylation in Sf9 Cells.

To determine the effects of kinase inhibitors on tau phosphorylation, Sf9 cells infected with baculovirus expressing htau23 were treated 36 hrs post-infection with 50 µM HD or flavopiridol for 5 hrs before being harvested. To obtain control tau samples with enhanced phosphorylation, the htau23 expressing Sf9 cells were treated with 0.2 µM okadaic acid for 5 hrs before harvest.

Tau Western Blotting.

Sf9 cells were infected with recombinant virus at a MOI of 1–5. Cell lysates were prepared in Hypotonic Lysis Buffer (HLB). After 15 min. centrifugation at 16,000 g, the supernatant was recovered and its NaCl concentration raised to 500 mM. It was then boiled for 10 min. and re-centriguged at 16,000 g for 15 min. Proteins (3 µg) were resolved by SDS-PAGE, transferred to a PVDF membrane, and Western blotted with the following antibodies: AT-8 (1:2000), AT-180 (1:1000), AT-100 (1:500), PHF-1 (1:600) and polyclonal anti-tau antibody K9JA.

Tau phosphorylation in vitro was performed using purified GSK-3β, and recombinant tau-32 as a substrate. After 30 min incubation in the presence of various HD concentrations, under the GSK-3β assay conditions described above, the kinase reaction was stopped by addition of Laemmli sample buffer. Tau was resolved by SDS-PAGE and its phosphorylation level visualised by autoradiography.

II/RESULTS

Kinase Inhibition Selectivity of Hymenialdisine

Enzyme activities were assayed as described in the Experimental Procedures section, in the presence of increasing HD concentrations. $IC_{50}$'s were calculated from the dose-response curves.–, no effect at the highest dose tested (in parentheses). The results are given in table 1.

TABLE 1

| Enzyme | $IC_{50}$ (nM) |
|---|---|
| cdk1/cyclin B | 22 |
| cdk2/cyclin A | 70 |
| cdk2/cyclin E | 40 |
| cdk3/cyclin E | 100 |
| cdk4/cyclin D1 | 600 |
| cdk5/p25 | 28 |
| cdk6/cyclin D2 | 700 |
| erk1 | 470 |
| erk2 | 2,000 |
| c-raf | >10,000 |
| MAPKK | 1,200 |
| c-Jun N-terminal kinase | 8,500 |
| protein kinase C α | 700 |
| protein kinase C β1 | 1,200 |
| protein kinase C β2 | 1,700 |
| protein kinase C γ | 500 |
| protein kinase C δ | 1,100 |
| protein kinase C ε | 6,500 |
| protein kinase C η | 2,000 |
| protein kinase C ζ | 60,000 |
| cAMP-dependent protein kinase | 8,000 |
| cGMP-dependent protein kinase | 1,700 |
| GSK3-β | 10 |
| ASK-γ (plant GSK-3) | 80 |
| Eg2 kinase | 4,000 |
| casein kinase 1 | 35 |
| casein kinase 2 | 7,000 |
| Insulin receptor tyrosine Kinase | 75,000 |
| c-src tyrosine kinase | 7,000 |
| c-abl tyrosine kinase | 4,000 |
| topoisomerase I | –(10,000) |
| topoisomerase II α | –(10,000) |

In the presence of 15 µM ATP, HD was found to inhibit CDK1/cyclin B, CDK2/cyclin A, CDK2/cyclin E, CDK3/cyclin E and CDK5/p35 with $IC_{50}$'s of 22, 70, 40, 100 and 28 nM, respectively (Table 1). As observed with olomoucine [29], roscovitine [15], indirubin-3'-monoxime [30], kenpaullone [31] and in contrast to flavopiridol [32], HD had limited effect on CDK4/cyclin D1 and CDK6/cyclin D2 ($IC_{50}$'s of 600 and 700 nM, respectively).

HD was next tested on a variety of highly purified kinases (Table 1). Kinase activities were assayed with appropriate substrates (histone H1, casein, myelin basic protein, peptides, . . . etc.), with 15 µM ATP (concentration chosen for practical reasons: comparison with previously published articles; high specificity of ATP) and in the presence of increasing concentrations of HD. $IC_{50}$ values are also presented in Table 1. Most kinases tested were poorly or not inhibited ($IC_{50}$>1 µM). However, two kinases, glycogen synthase kinase-3β (GSK-3β) and casein kinase 1 (CK1) were strongly sensitive to HD ($IC_{50}$'s of 10 and 35 nM, respectively)

Inhibition of CDK1/Cyclin B by HD Analogues

CDK1/cyclin B was assayed as described under the Experimental Procedures section in the presence of increasing concentrations of HD and analogues. Activity is presented as % of maximal activity, i.e. measured in the absence of inhibitors. The results are given on FIG. 2.

In Vitro Assay of HD Sensitive Kinases with Relevant Substrates

The HD-sensitive kinases were also assayed in vitro with physiologically relevant substrates: a fragment of presenilin-2 [25] for casein kinase 1, Pak1 [17] for CDK5/p35, the insulin-receptor substrate IRS-1 [33] or tau for GSK-3β. The results are illustrated on FIGS. 3–5.

FIG. 3 illustrates the inhibition effect of HD on the phosphorylation of presenilin-2 by casein kinase 1 in vitro. A bacterially-expressed fusion protein between presenilin-2 and maltose-binding protein (PS-2.MBP) was phosphorylated in vitro with casein kinase 1 in the presence of increasing HD concentrations and resolved by SDS-PAGE, followed by autoradiography.

FIG. 4 illustrates the inhibition effect of HD on Pak1 phosphorylation by CDK5/p35 in vitro and in vivo. Rat embryo cortical neurones were exposed to various HD concentrations for 1 hr. Pak1 was then immunoprecipitated and its kinase activity towards histone H4 measured. The upper panel shows the level of H4 phosphorylation following SDS-PAGE of the substrate. Numbers correspond to the quantification of the autoradiography. Western blots show amounts of Pak1 (lower panel) and p35. An increase in p35 levels as a consequence of CDK5 inhibition. FIG. 5 illustrates the inhibition effect of the phosphorylation by tau phosphorylation by GSK-3β in vitro and in vivo.

FIG. 5A gives the results of the following experiments: Bacterially-expressed recombinant human tau was phosphorylated in vitro with GSK-3β in the presence of increasing HD concentrations and resolved by SDS-PAGE, followed by autoradiography.

In experiments whose results are given on FIG. 5B, Sf9 cells expressing htau23 were left untreated (−), or exposed to okadaic acid (OA), hymenialdisine (HD) or flavopiridol (FL) for 5 hrs. Cell lysates (3 µg htau23) were resolved by SDS-PAGE, stained with Coomassie blue or immunoblotted with various antibodies: K9JA (a pan-tau antibody) recognizes all preparations which contain tau; AT8, AT180 and PHF1 are specific for different phosphorylated SP or TP motifs; AT100 recognizes tau phosphorylated at T212 and S214, a highly specific reaction for Alzheimer tau.

The sensitivity of the kinases towards HD remained quite comparable to the sensitivity of the same kinases assayed with more artificial substrates.

Inhibition of CDK1, CDK5 and GSK-3β and CK1 by Hymenialdisine Analogues.

Some natural HD-related compounds isolated from marine sponges and some synthetically modified HD analogues on CDK1/cyclin B, CDK5/p35, GSK-3β and CK1 were tested. The results are given on FIG. 2 and Table 2. Numbers refer to structures shown in FIG. 1. Enzyme activities were assayed as described in the Experimental Procedures section, in the presence of increasing HD concentrations. $IC_{50}$'s were calculated from the dose-response curves. When no inhibitory effect was observed (−), the highest concentration tested is given in parentheses.

TABLE 2

| N° | Compound | IC50 (nM) towards | | | |
|---|---|---|---|---|---|
| | | CDK1/cyclin B | CDK5/p25 | GSK3-β | CK 1 |
| 1 | hymenialdisine | 22 | 28 | 10 | 35 |
| | hymenialdisine-platinum complex | 30 | 200 | 130 | 1,000 |
| | diacetylhymenialdisine | 130 | 1,500 | 160 | 550 |
| | diacetyldebromohymenialdisine | 1,300 | 3,000 | 600 | 1,100 |
| 4 | stevensine/odiline | 70,000 | −(100,000) | −(100,000) | −(100,000) |
| 5 | axinohydantoin | 4,000 | 7,000 | 3,000 | 4,500 |
| 8 | dibromophakellstatin | −(10,000) | −(100,000) | >10,000 | −(10,000) |
| 9 | agelastatin A | −(100,000) | −(100,000) | 12,000 | −(100,000) |
| 10 | dibromocantharelline | >100,000 | >100,000 | 3,000 | −(100,000) |
| 11 | dispacamide A | −(100,000) | −(100,000) | −(100,000) | −(100,000) |
| 12 | clathrodin | >100,000 | >100,000 | 10,000 | −(100,000) |
| 13 | hymenidin | >100,000 | 4,000 | 12,000 | >100,000 |
| 14 | oroïdin | >100,000 | 50,000 | 20,000 | >100,000 |
| 15 | agelongine | −(100,000) | −(100,000) | −(100,000) | −(100,000) |
| 6 | dibromoageliferin | >100,000 | >100,000 | 11,000 | −(100,000) |
| 7 | sceptrin | −(100,000) | −(100,000) | −(100,000) | −(100,000) |

HD remained the most active compound. Interestingly, dibromocantharelline (10) displayed a significant inhibitory effect towards GSK-3β ($IC_{50}$ of 3 µM). Hymenidin (13) was selective for CDK5.

Hymenialdisine is a Competitive Inhibitor of ATP Binding

To investigate the mechanism of HD action, kinetic experiments were performed by varying both ATP levels and HD concentrations (FIG. 6A). Double-reciprocal plotting of kinetic data from assays of CDK1/cyclin B protein kinase activity at different concentrations of hymenialdisine.

Enzyme activities were assayed as described under the Experimental Procedures section. Results illustrated by FIG. 6A: 1/v vs 1/ATP primary plot. ATP concentrations in the reaction mixture varied from 0.05 to 0.25 mM, concentration of histone H1 was kept constant at 0.7 mg/ml. Inset displays secondary re-plots of slopes versus concentration from primary plots. Apparent inhibition constant ($K_i$) is indicated by an arrow. Results illustrated by FIG. 6B: Hymenialdisine does not release cyclin B from CDK1. p9$^{CKShs1}$-sepharose—immobilised CDK1/cyclin B was exposed to HD for 30 min., washed and analysed by western blotting with anti-cyclin B and anti-PSTAIRE antibodies.

The data demonstrates that HD acts as a competitive inhibitor for ATP. The linearity of the slope versus HD concentration re-plots qualifies HD as a linear inhibitor (FIG. 6A, inset). The apparent inhibition constant (Ki) was 50 nM. HD does not act by displacing cyclin B from CDK1 (FIG. 6B): CDK1/cyclin B immobilised on p9$^{CKShs1}$-sepharose was exposed to high HD concentrations; the beads were then extensively washed, prior to Western blot analysis. Both subunits were still detectable together.

Crystal Structure of the CDK2/Hymenialdisine Complex

The structure of a CDK2 crystal soaked in HD was determined and refined at 2.1 Å resolution. Treatment with a cross-linking agent, prior to soaking, was necessary to prevent the crystal from cracking. Details of the structure determination are given in Table 3.

TABLE 3

| Space group | $P2_12_12_1$ |
| --- | --- |
| Cell dimensions (Å) | |
| a | 53.39 |
| b | 70.67 |
| c | 72.26 |
| Number of measurements (I/σ(I) > 1.0) | 51723 |
| Unique reflections | 16264 |
| Completeness of data to 2.10 Å (%) | 98.1 |
| $R_{sym}^*$ (%) | 4.8 |
| Resolution range (Å) | 30–2.10 |
| $R_{factor}^{**}$ (%) | 19.4 |
| $R_{free}$† (%) | 26.2 |
| B values# (Å$^2$) | |
| Main chain | 32.8 |
| Side chains | 35.5 |
| Inhibitor | 46.9 |
| Waters | 35.2 |
| Ethylene glycols | 52.0 |
| Deviations observed | |
| Rms. bond lengths (Å) | 0.008 |
| Rms. bond angles (°) | 1.32 |
| Number of water molecules | 84 |

*$R_{sym} = \Sigma | I(h) - <I(h)> |/\Sigma I(h)$, with I(h), observed intensity and <I(h)>, mean intensity of reflection h over all measurement of I(h).
**$R_{factor} = \Sigma | F_0 - F_c |/ \Sigma (F_0)$, the sums being taken over all reflections with F/σ(F)>1 cutoff.
†$R_{free} = R_{factor}$ for 10% of the data, which were not included during crystallographic refinement.
B values = Average B values for all non-hydrogen atoms.

The final model consists of 274 amino acid residues, one bound HD, 85 solvent molecules and four molecules of ethylene glycol, with a crystallographic R-factor of 19.2% ($R_{free}$ of 26.7%) and good geometry. Residues 36–44 and 149–163 of CDK2, that are part of two highly flexible loops, were left out from the final model due to weak or missing electron density. All non-glycine residues in the CDK2 model have main chain torsion angles that lie well within the energetically favorable regions of the Ramachandran plot [26], except for two residues, Glu-73 and Arg-126, that have backbone conformations falling just outside the "additional allowed" region in φ-ψ space.

A stereo view of the electron density for HD is given on FIG. 7. HD could be unambiguously localized in a Fourier difference map confirming that this inhibitor also binds in the ATP-binding pocket (FIG. 7A). A schematic representation of the binding site interactions is shown in FIGS. 7B and 8.

FIG. 7A is a stereo diagram showing the refined structure of HD in the ATP binding pocket of CDK2. Inferred hydrogen bonds are shown as thin dotted lines.

FIG. 7B is a schematic illustration of the interactions between CDK2 and HD. Protein side chain contacts are indicated by lines connecting to the respective residue box while interactions to main-chain atoms are shown as lines to the specific main-chain atom. Van der Waals contacts are indicated by dotted lines, and hydrogen bonds by broken lines.

The pyrroloazepine double ring system of HD fills a shallow hydrophobic pocket formed by Ile-10, Val-18, Ala-31, Val-64, Phe-80, and Leu-134, making several van der Waals contacts with the side chain atoms of these residues. In addition three hydrogen bonds are formed with the backbone of CDK2, between the N1 atom of the pyrrole ring and the carbonyl oxygen of Leu-83, between the O1 carbonyl oxygen of azepine ring and the backbone amide of Leu-83, and between the N2 amide of the azepine ring and the carbonyl oxygen of Glu-81. The bromine atom bound to the pyrrolo ring of HD points towards the outside of the ATP-binding pocket, were it is partly exposed to solvent, but also packed against the main chain carbonyl oxygen's of Ile-10 and His-84, and the side chains of Ile-10 and Leu-134. Binding of the guanidine ring system of HD involves a few van der Waals contacts, mainly with the side chain of Val-18, in addition to one direct and two water-mediated hydrogen bonds. The direct hydrogen bond is formed between the N5 amino group of the guanidine and one of the side chain oxygen's of Asp-145. The two water-mediated hydrogen bonds are between the O2 of HD and the main chain NH of Asp-145, and between the N5 of HD and the main chain carbonyl of Gln-131. Comparison with the apo-CDK2 and CDK2/ATP structures reveals a large movement of Asp-145 upon binding of HD, consisting of a 1 Å shift of the Cα atom, and a rotation of the side chain of about 90° around the Cα–Cβ bond away from the HD guanidine ring. All other residues in contact with the inhibitor have conformations very similar to those observed in the apo-CDK2 and CDK2/ATP structures.

Comparison of CDK2/Hymenialdisnie with other CDK2/Inhibitor Complexes

To provide a structural basis for understanding the potency of HD, the structure of the CDK2/HD complex was compared to the structures of CDK2 complexed with ATP, staurosporine, flavopiridol and with the purine analogs olomoucine, roscovitine and purvalanol, as well as with the structure of the cyclin A/CDK2/ATP complex. Stereo views showing the comparison are given on FIG. 9.

FIG. 9A gives the superposition of HD (black bonds) on ATP (white bonds) in apo-CDK2 and on ATP (yellow bonds) in cyclin A-CDK2.

FIG. 9B gives the superposition of HD on olomoucine (white) and purvalanol.

FIG. 9C gives the superposition of HD on flavopiridol. The CDK2 backbone atoms of residues 81–84, and the side chain of Asp-145 in the CDK2/HD complex are shown in ball-and-stick representation with black bonds. The same residues from the superposed CDK2-ligand complex are shown as bonds. In A) the thin bonds refer to the apo-enzyme, the thick bonds to the cyclin A-CDK2 dimers.

The hydrophobic double ring system of HD binds at approximately the same position in CDK2 as the purine ring of ATP in the CDK2/ATP complex, similar to the positions of the double ring-systems in the other CDK2/inhibitor complexes (FIG. 9). Although the orientation of the different double ring systems varies significantly among the different inhibitors, it is restrained by the necessity to provide optimal shape complementarity with the shallow ATP-purine binding pocket while allowing the formation of a number of hydrogen bonds with the backbone of residues 81–83 at the cross-over connection in CDK2. The hydrogen bonding interactions in the CDK2/HD complex seem to be the most favorable of all the CDK2/inhibitor complexes studied so far. The hydrogen bonds between N2 and the peptide oxygen of Glu-81, and between O1 and the peptide amide of Leu-83 resemble closely those between the adenine base of ATP and CDK2 and those in the CDK2/inhibitor complexes with staurosporine and flavopiridol. The third hydrogen bond in the CDK2/HD complex with the main chain carbonyl of Leu-83, is absent in these complexes, and can be observed only in the complexes with the three purine-based inhibitors olomoucine, roscovitine and purvalanol. Like HD these latter three inhibitors also form three hydrogen bonds with the crossover connection, but their interaction with the Glu-81 peptide oxygen is much weaker, involving a rare C—H—O hydrogen bond with the acidic C8 atom of the purine ring.

The bromine atom of HD is bound close to a region in CDK2 that in the other CDK2/inhibitor complexes is occupied by a benzyl group. Binding of a hydrophobic group in this region, where it can pack against the side chains of Ile-10, Phe-82 and the backbone of residues 82–84, is important for increasing the specificity of inhibitors for CDK2. Although the bromine in HD can not provide the same number of interactions as a benzyl ring, the presence of this atom in HD is likely to contribute significantly to its binding affinity and specificity towards CDK2, as can been seen from the inhibitory activities of various HD-analogs in Table 2 and FIG. 2.

Interesting also is the region of CDK2 occupied by the guanidine ring of HD. A superposition with the other CDK2/inhibitor complexes shows that only the flavopiridol and staurosporine inhibitors have groups bound in this region of CDK2, which partly overlaps with the pocket where the α-phosphate of ATP is bound. Comparison of the structure of the CDK2/HD complex with that of the CDK2/flavopiridol complex [34] reveals a number of striking similarities between the binding modes of these structurally diverse inhibitors. The O2 carbonyl oxygen of HD is located close to the position of the O7 hydroxyl group of the flavopiridol, which emanates from the benzopyran ring bound at the ATP-purine binding pocket. In both inhibitors the oxygen atoms make a water-mediated hydrogen bond with the main chain amide of Asp-145. Furthermore, the N5 amino group at the guanidine ring of HD is located near to the position of the positively charged amine group of the piperidinyl ring in the CDK2/flavopiridol complex. Both atoms are in hydrogen bond distance with the side chain carboxylate of Asp-145. The energetically favorable interaction between the positively charged amine group of the flavopiridol and the negatively charged carboxylate of Asp-145 would make an important contribution to the binding strength of this inhibitor to CDK2. A similar interaction seems possible in the CDK2/HD complex, as under physiological conditions the guanidine ring is likely to be at least partly protonated at N3, thus providing a (partly) positive charge delocalized between N3, C11, N4 and N5. Also the movement of Asp-145 is conserved in both CDK2/inhibitor complexes. It is also seen in the indirubin-5-sulphonate/CDK2 structure. Asp-145 is part of the conserved DFG motif found in most protein kinases. Although significantly different from those in the CDK2/ATP complex, the position and conformation of Asp-$145$ in both CDK2/inhibitor complexes is in fact very similar to those in the functionally more relevant cyclin A/CDK2/ATP complex (FIG. 9A).

In Vitro Inhibition of Presenilin Phosphorylatio

The effects of HD on the in vitro and in vivo phosphorylation of various protein substrates relevant to Alzheimer's disease were also investigated The large hydrophilic loop of presenilin-2 between transmembrane domains 6 and 7 is a substrate for both casein kinase 1 and 2 in vitro; this domain is phosphorylated in vivo [25]. Using a presenilin-2-MBP fusion protein as an in vitro substrate for CK1. a dose-dependent inhibition of presenilin-2 phosphorylation by HD was observed (FIG. 3). MBP alone was not phosphorylated by CK1.

In Vitro and In Vivo Inhibition of Pak1 Phosphorylation by Neuronal CDK5/p35.

Among the physiological substrates of CDK5/p35 is the neuronal kinase Pak1 [17]. Both Pak1 and p35 associate with Rac, a small GTPase of the Rho family. Pak1 phosphorylation by CDK5/p35 results in an inhibition of the Pak1 kinase activity. Roscovitine inhibits CDK5/p35 and the resulting down-regulation of Pak1 both in vitro and in vivo. These experiments were repeated with HD (FIG. 4). First CDK5/p35 was immunoprecipitated from P02 rat cortices and its kinase activity towards GST-Pak1K299 (kinase-dead Pak1 mutant) in the presence of HD, roscovitine or DMSO was assayed as [17]. A dose-dependent inhibition of CDK5 by HD was observed ($IC_{50}$ between 10 and 100 nM) (FIG. 4A). In vivo experiments were next performed using cultured neurons obtained from E18 rat embryo cortices (FIG. 4B). HD was added when the cultures were 4 days old and left on the cells for 1 hour. DMSO was used as a control. The cells were then lysed on ice in STM buffer and the membrane fraction isolated [17]. Pak1 was then immunoprecipitated and assayed using histone H4. The amount of H4 phosphorylation, measured by the intensity of the bands on the autoradiography film, was quantitated with NIH imaging program. As controls for loading anti-Pak1 and anti-p35 western blots were performed. As previously shown [35], p35 increases in amount with the extent of CDK5/p35 kinase inhibition. An increase in Pak1 activity was observed, consistent with an inhibition of endogenous CDK5 activity (FIG. 4B).

HD Inhibits MAP-1B Phosphorylation by GSK-3 in Cerebellar Granule Cell Neurons

GSK-3β is inhibited by both WNT-7a and lithium in cerebellar granule cell neurons. [49,50]. WNT-7a and lithium induce axonal remodelling and loss of a phosphorylated form of MAP-1B, a microtubule associated protein involved in axonal outgrowth. As GSK-3β phosphorylates MAP-1B at a site recognised by the antibody SMI-31 inhibition of GSK-3β by WNT or lithium results in the loss of a phosphorylated MAP-1B, MAP-1B-P. To examine the effect of HD on neuronal morphology and MAP-1B phosphorylation cerebellar granule cells were cultured in different concentrations of HD.

The results are given on FIG. 10. Double immunofluorescence staining for GAP43 and MAP-1B-P shows that MAP-1B-P is present along the axon (A and B). 20 h treatment with 10 μM HD has no obvious effect on cell morphology (C), or MAP-1B-P (D). Arrows indicate the same cells. 50 μM HD treatment induces axonal spreading, shortening of the axon (E) and loss of MAP-1B-P from axonal processes (F). Arrows indicate the same cells. 100 μM HD treatment causes a more dramatic change in cell morphology with spreading and branching along the axon, an increased number of filopodia and shortening of the axon (G). MAP-1B-P is lost from most of the axonal processes (H). Arrows indicate axons where MAP-1B-P is lost. Bar=20 μM.

Western blotting analysis of cell lysates shows a gradual decrease in MAP-1B-P in response to increasing doses of HD (I).

In control cells with long processes and very few filopodia (FIG. 10A), MAP-1B-P is present along the entire length of the axon (FIG. 10B). At low concentrations (1 μM, 10 μM, 25 μM) HD had no noticeable effect on the morphology of the cells (FIG. 10C), or the distribution of MAP-1B-P (FIG. 10D). However, 50 μM HD treatment induced axonal spreading and branching and a shortening of axon length (FIG. 10E), with a concomitant loss of MAP-1B-P from most of the axonal processes (FIG. 10F). Treatment of cultures with 100 μM HD caused a more dramatic change in cell morphology characterised by extensive branching and spreading, shortening of axon length and an increased number of filopodia were observed (FIG. 10G), together with loss of MAP-1B-P from processes (FIG. 10H). The axonal remodelling observed was associated with a loss of stable microtubules from spread areas of the axons. HD induces the loss of MAP-1B-P in a dose-dependent manner as determined by Western blotting (FIG. 10I). This effect is similar to that observed with lithium or WNT-7a treatment [37]. As it was shown that HD inhibits GSK-3β directly, said results suggest that the loss of MAP-1B-P and axonal remodelling induced by HD is a consequence of GSK-3β inhibition in cultured neurons.

Inhibition of Tau Phosphorylation by GSK-3 In Vivo and In Vitro

The microtubule-binding protein tau is the substrate of several kinases, including GSK-3β and CDK5/p35. Bacterially-expressed recombinant human tau was indeed phosphorylated in vitro by GSK-3β and this phosphorylation was inhibited in a dose-dependent manner by HD, with an $IC_{50}$ around 33 nM (FIG. 5A). The effect of HD on the in vivo phosphorylation of human tau23 expressed in Sf9 cells was then investigated (FIG. 5B). Cells were left untreated (−), or exposed to 0.2 μM okadaic acid (OA), 50 μM HD or 50 μM flavopiridol (FL), a CDK inhibitor which also inhibits GSK-3β. Htau23 was resolved by SDS-PAGE followed by immunoblotting with various antibodies. K9JA (a pan-tau antibody) recognizes all preparations which contain tau. AT8, AT180 and PHF1 are specific for different phosphorylated SP or TP motifs, respectively Ser202 & Thr205, Thr231 & Ser235 and Ser396 & Ser404 (as numbered in htau40, the longest human tau isoform). AT100 recognizes tau phosphorylated at T212 and S214; this reaction is highly specific for Alzheimer tau but occurs in Sf9 cells as well, provided both sites are phosphorylated. The disappearance of AT100 signal following treatment with HD or flavopiridol indicates that both compounds are able to inhibit GSK-3β like activity in Sf9 cells.

III Manufacture of CDKs1,2,5, GSK-3β and Casein Kinase 1 Inhibitors

Liquid Formulation

A suspension or solution of HD is prepared by adding 100 to 1000 mg of HD to a liquid carrier, such as ethanol, glycerine, a non-aqueous solvent, such as polyethylene glycol, oils, or water with a suspending agent, perservative, flavoring or coloring agent, the amount of liquid carrier being adjusted to obtain the required concentration in active principle.

Tablet

The 2 bromo HD derivative is incorporated to a carrier, such as magnesium stearate, starch, lactose, sucrose or cellulose, and compressed.

The respective amounts are choosen dependig on the desired concentration in the active principe.

IV Study of the Cellular Effects of HD

Methods

NCI Disease-Oriented In Vitro Screen

Sixty human tumor cell lines comprising 9 tumor types (Boyd and Paull, 1995) were cultured for 24 hr prior to a 48 hr continuous exposure to 0.01–100 μM roscovitine. A sulforhodaminine B protein assay was used to estimate the cytotoxicity.

Thymidine uptake. HT29-18-C1 cells were cultured in a 24 well plate at a cell density of 2.105 cells/500 μl medium/well. Subconfluemt cells were rinsed and placed in serum free medium for 48 h for the starvation-synchronization. The release from growth arrest was performed by addition of 5% serum in the presence of HD. 2 μCi of methyl-3H thymidine (specific activity 50 Ci/mMol) (ICN Biomedical) were added to each well during the last 4 h of a 24 h treatment period. Cells were then washed with PBS and treated with cold 5% trichloracetic acid for 45 min at 4° C. Cells were rinsed with water and solubilized with 0.3 M NaOH for 1 h at 37° C. The radioactivity was measured with a Beckman beta counter.

Cell culture and treatments. HT29-18-C1, a subclone of the human colon adenocarcinoma cell line HT29, was cultured in Dulbecco's modified Eagle's medium (Gibco-BRL) supplemented with 10% FCS, 2 mM L-glutamine (Eurobio) and 50 mg/ml gentamycin (Gibco-BRL) at 37° C., 10% CO2. Cells were synchronized by serum deprivation for 48 h. They were then released from growth arrest by the addition of 5% fetal calf serum (FCS). HD, prepared in DMSO, was added immediately to the medium, for 24 h and at final concentrations ranging from 0 to 80 μM. In some experiments HD was added 22 h after serum addition for an additional 24 h. In other experiments HD was added to unsynchronised cells. Cells were then washed and cultured in 5% FCS medium and counted or analysed by FACS at different times.

Cell counts and flow cytometric cell cycle analysis. Cell were counted with a hemocytometer. Cell cycle distribution was analysed by flow cytometry. The adherent cells ($1.10^6$) were trypsinised and fixed in cold 70% ethanol for 4 h. Fixed cells were washed with PBS and incubated with 5 μg of RNAse A (Sigma Chemicals) per ml and stained with 25 μg/ml of propidium iodine (Aldrich) for 1 h at 37° C. The stained cells were analysed on a FACScan cytofluorimeter using the cellFit Software program (Becton Dickinson Immunocytometry Systems).

Results

Cellular Effects of Hymenialdisine: Inhibition of Proliferation

HD (0.01–100 µM; 48 hr exposure) was tested on the NCI disease-oriented in vitro screen, i.e. 60 human tumor cell lines comprising 9 tumor types (leukemia, non-small cell lung cancer, colon cancer, central nervous system cancer, melanoma, ovarian cancer, renal cancer, prostate cancer, breast cancer). All cell lines displayed a similar sensitivity to HD. The average $IC_{50}$ was 15.1 µM (roscovitine: 16 µM (Meijer et al., 1997); olomoucine: 60.3 µM (Abraham et al., 1995)). No correlation was observed between the sensitivity of cell lines to roscovitine and the presence of wild-type or mutated p53.

indicate the % of cells in the different the cell cycle phases. FIG. 10B gives the kinetics of S phase accumulation in HD-treated cells. Serum was added at time 0 to serum-starved HT29-18-C1 cells which were simultaneously treated or not with 10 µM HD for the following 24 h. Cell cycle distribution was analysed every 24 h for a 72 h period.

Fluorescent-activated cell sorter (FACs) analysis revealed that HD treatment lead to an accumulation of cells in S phase relative to the untreated cells. In the absence of HD, serum-stimulated cells readily proceeded to enter G2/M (FIG. 10A). In contrast, HD-treated cells failed to proceed into G2/M following serum stimulation but remained arrested in S phase. The effect of HD on cell cycle distribution of the HT29-18-C1 culture was also investigated over time (FIG.

| Cellular Properties | | |
|---|---|---|
| Inhibitor of cell proliferation | | |
| Compound | IC50 (µg/ml) on P388 cell line | |
| Hymenialdisine | 3.2 | (9.9 µM) |
| Diacetylhymenialdisine | 0.56 | (1.7 µM) |

| | IC50 (µg/ml) | | |
|---|---|---|---|
| human cancer cell line | dibromophakellin | hymenialdisine | dibromophakellstatin |
| ovary, OVCAR-3 | 15.7 | 1.8 | 0.46 |
| brain, SF-295 | 18.8 | 38.9 | 1.5 |
| kidney, A498 | 17.8 | 24.7 | 0.21 |
| lung, H460 | 22.0 | 42.0 | 0.62 |
| colon, KM20L2 | 20.1 | 8.5 | 0.11 |
| melanoma, SK-MEL-5 | 17.0 | 5.7 | 0.11 |

Cellular Effects of Hymenialdisine: Arrest in S Phase and at the G2/N Transition Hymenialdisine Causes Growth Inhibition of HT29-18-C1.

HT29-18-C1 cells were synchronised in G1 by serum deprivation. 5% FCS was added at time 0 and cells were simultaneously treated (o) or not (o) exposed to 10 µM HD. During 24 h and thereafter cultured in 5% FCS-containing medium. Cell number was determined every 12 h for a 72 h period using a hemocytometer. The kinetics of growth inhibition are given on FIG. 9A. HD treatment resulted in strong growth inhibition as monitored by the reduced increase in cell number over a 72 h period as compared to the control. Serum-treated cells (time 0) were exposed to various HD concentrations and counted after 24 h. The results are given on FIG. 9B. The number of non-serum stimulated cells (▪) is indicated for comparison. The inhibitory effect was HD dose-dependent, with an $IC_{50}$ of 5 µM (FIG. 9B). Trypan blue dye exclusion indicated little toxicity associated with 10 and 80 µM HD at 24 h (>95% and 90% viability, respectively). This antiproliferative effect of HD appears to be reversible. In fact, cells slowly began to proliferate again after 72 h culture.

Hymenialdisine Causes an S Phase Arrest.

The results concerning the cell cycle distribution of HD-treated cells are given on FIG. 10A. HT29-18-C1 were serum-starved for 48 hr. 5% serum was then added (time 0) and cells were simultaneously treated or not with 5 or 40 µM HD for the next 24 h. Cells were then fixed and their cell cycle phase status was determined by FACscan analysis as described in the Experimental Procedures section. Numbers 10B). Synchronized cells were placed in 5% FCS medium in the presence or absence of 10 µM HD for 24 h. Cells were then cultured in 5% FCS medium for another 48 h. In agreement with cell counts, its was observed that HD inhibits cell proliferation over 72 h of cell culture with an accumulation of cells in S phase (FIG. 10B). Hymenialdisine causes a G2/M arrest.

In another type of experiments, HT29-18-C1 were serum-starved for 48 hr. 5% serum was added at time 0 and 10 µM HD was added 22 hr later. The cell cycle distribution was determined 14 h later, i.e. 36 h after serum stimulation, by FACscan analysis as described in the Experimental Procedures section. In this case, the cells had a chance to enter the S phase and HD treatment lead to an accumulation of cells in G2/M (FIG. 11).

REFERENCES

1. Dunphy, W. G. (editor) (1997) Cell cycle control. Methods in Enzymology, Academic Press, vol. 283, 678 pp.
2. Morgan, D. (1997) Cyclin-dependent kinases: engines, clocks, and microprocessors. *Annu Rev Cell Dev Biol* 13, 261–291.
3. Vogt, P. K., & Reed, S. I. (1998) Cyclin dependent kinase (CDK) inhibitors. *Current Topics in Microbiology & Immunology*, Springer Verlag, 169 pp.
4. Grays, N S, Détivaud, L, Doerig, C, & Meijer, L (1999) ATP-site directed inhibitors of cyclin-dependent kinases. *Curr Medicin Chem* 6, 859–875.
5. Cimino, G., de Rosa, S., de Stefano, S., Mazzarella, L., Puliti, R., & Sodano, G (1982) Isolation & X-ray crystal structure of a novel bromo-compound from two marine sponges. *Tetrahedron Lett* 23, 767–768.
6. Pettit, G. R., et al., Boyd, M. R. (1997) Antineoplastic agents. 362. Isolation and X-ray crystal structure of dibromophakellstatin from the Indian Ocean sponge *Phakellia mauritiana. J Nat Prod* 60, 180–183.
7. Pettit, G. R., et al., & Camou, F. (1990) Antineoplastic agents. 168. Isolation and structure of axinohydantoin. *Can J Chem* 68, 1621–1624.
8. D'ambrosio, M., et al., & Pietra, F. (1993) Agelastatin A, a new skeleton cytotoxic alkaloid of the oroidin family. Isolation from the Axinellid sponge *Agelas dendromorpha* of the Coral Sea. *J Chem Soc, Chem Commun* 1993, 1305–1306.
9. De Nanteuil, G., et al., & Laboute, P. (1985) Invertébrés marins du lagon Neo-Caledonien-V: Isolement et identification des métabolites d'une nouvelle espèce de spongiaire, *Pseudaxinyssa Cantharella. Tetrahedron* 41, 6019–6033.
10. Cafieri, F., Fattorusso, E., NMangoni, A., Taglialatela-Scafati O. (1995) A novel bromopyrrole alkaloid from the sponge *Agelas longissima* with antiserotonergic activity. *Bioorganic & Medicinal Chem Lett* 5, 799–804.
11. Cafieri, F., Fattorusso, E., Mangoni, A., & Tagliatela-Scafati, O. (1996) Dispacamides, anti-histamine alkaloids from Carribean *Agelas* sponges. *Tetrahedron Lett* 37, 3587–3590.
12. Walker, R. P., Faulkner, D. J., Van Engen, D., & Clardy, J. (1981) Sceptrin, an antimicrobial agent from the sponge *Agelas sceptrum. J Am Chem Soc* 103, 6772–6773.
13. Garcia, E. E., Benjamin, L. E., & Fryer, R. I. (1973) Reinvestigation into the structure of oroidin, a bromopyrrole derivative from marine sponge. *J C S Chem Comm* 1973, 78–79.
14. Albizati, K. F. & Faulkner D. J. (1985) Stevensine, a novel alkaloid of an unidentified marine sponge. *J Organic Chem* 50, 4163–4164.
15. Meijer, L., et al., & Moulinoux, J. P. (1997) Biochemical and cellular effects of roscovitine, a potent and selective inhibitor of the cyclin-dependent kinases cdc2, cdk2 & cdk5. *Eur J Biochem* 243, 527–536.
16. Borgne, A., Ostvold, A. C., Flament, S., & Meijer, L. (1999) Intra-M Phase-promoting factor phosphorylation of cyclin B at the prophase/metaphase transition. *J Biol Chem* 274, 11977–11986.
17. Nikolic, M., Chou, M. M., Lu, W., Mayer, B. J., & Tsai, L.-H. (1998) The p35/cdk5 kinase is a neuron-specific Rac effector that inhibits Pak1 activity. *Nature* 395, 194–198.
18. Hughes, K., Pulverer, B. J., Theocharous, P., & Woodgett, J. R. (1992) Baculovirus-mediated expression and characterisation of rat glycogen synthase kinase-3 beta, the mammalian homologues of the *Drosophila melanogaster* zeste-white 3sgg homeotic gene product. *Eur J Biochem* 203, 305–311.
19. Rosenblatt, J., De Bondt, H. L., Jancarik, J., Morgan, D. O., & Kim, S.-H. (1993) Crystal structure of cyclin-dependent kinase 2. Purification and crystallization of human cyclin-dependent kinase 2. *J Mol Biol* 230, 1317–1319.
20. Otwinowski, Z., & Minor, W. (1997) Processing of X-ray Diffraction Data Collected in Oscillation Mode. *Methods Enzymol* 276A, 307–326.
21. Collaborative Computational Project, Number 4 The CCP4 Suite: Programs for Protein Crystallography. *Acta Crystallogr* D50, 760–763.
22. Brünger, A. T. (1993) X-PLOR, Version 3.1. A system for protein crystallography and NMR; Yale University Press: New Haven, Conn.
23. Mattia, C. A., Mazzarella, L., & Puliti, R. (1982) 4-(2-amnino-4-oxo-2-imidazolin-5-ylidene)-2-bromo-4,5,6,7-tetrahydropyrrolo-[2,3-c]azepin-8-one methanol solvate: a new bromo compound from the sponge *Acanthella aurantiaca. Acta Crystallogr* B38, 2513–2515.
24. Laskowski, R. A., MacArthur, M. W., Moss, D. S., & Thornton, J. M. (1993) PROCHECK: a program to check the stereochemical quality of protein structures. *J Appl Crystallogr* 26, 283–291.
25. Walter, J., Grunberg, J., Schindzielorz, A., & Haass, C. (1998) Proteolytic fragments of the Alzheimer's disease associated presenilins-1 and -2 are phosphorylated in vivo by distinct cellular mechanisms. *Biochemistry* 37, 5961–5967.
26. Hatten, M. E. (1985) Neuronal regulation of astroglial morphology & proliferation in vitro. *J. Cell Biol.* 100, 384–396.
27. Goedert, M., Spillantini, M., Jakes, R., Rutherford, D., & Crowther, R. A. (1989) Multiple isoforms of human microtubule-associated protein-tau: sequences & localization in neurofibrillary tangles of Alzheimers-disease. *Neuron* 3, 519–526.
28. Biernat, J., Gustke, N., Drewes, G., Mandelkow, E.-M., Mandelkow, E. (1993). Phosphorylation of serine 262 strongly reduces the binding of tau protein to microtubules: Distinction between PHF-like immunoreactivity and microtubule binding. *Neuron* 11, 153–163.
29. Vesely, J., et al., & Meijer, L. (1994) Inhibition of cyclin-dependent kinases by purine derivatives. *Eur. J Biochem* 224, 771–786.
30. Hoessel, R., et al., & Meijer, L. (1999) Indirubin, the active constituent of a Chinese antileukaemia medicine, inhibits cyclin-dependent kinases *Nature Cell Biology* 1, 60–67.
31. Zaharevitz, D., et al., & Sausville, E. A. (1999) Discovery and initial characterization of the paullones, a novel class of small-molecule inhibitors of cyclin-dependent kinases. *Cancer Res* 59, 2566–2569.
32. Carlson, B. A., Dubay, M. M., Sausville, E. A., Brizuela, L., & Worland, P. J. (1996) Flavopiridol induces G1 arrest with inhibition of cyclin-dependent kinase (CDK) 2 & CDK4 in human breast carcinoma cells. *Cancer Res* 56, 2973–2978.
33. Eldar-Finkelman, H. & Krebs, E. G. (1997) Phosphorylation of insulin receptor substrate 1 by glycogen synthase kinase 3 impairs insulin action. *Proc Natl Acad Sci USA* 94, 9660–9664.
34. De Azevedo, W. F., Mueller-Dieckmann, H. J., Schulze-Gahmen, U., Worland P. J., Sausville, E., & Kim, S.-H. (1996) Structural basis for specificity and potency of a flavonoid inhibitor of human CDK2, a cell cycle kinase. *Proc Natl Acad Sci USA* 93, 2735–2740.
35. Patrick, G. N., Zhou, P., Kwon, Y. T., Howley, P. M., & Tsai, L.-H. (1998) p35, the neuronal activator of CDK5, is degraded by the ubiquitin-proteasome pathway. *J Biol Chem* 273, 24057–24064.
36. Lucas, F. R. & Salinas, P. C. (1997) WNT-7a induces axonal remodelling and increases synapsin I levels in cerebellar neurons. *Dev. Biol.* 193, 31–44.
37. Lucas, F. R., Goold, R. G., Gordon-Weeks, P. R., & Salinas, P. C. (1998) inhibition of GSK-3β leading to the loss of phosphorylated MAP-1B is an early event in axonal remodeling induced by WNT-7a or lithium. *J Cell Sci* 111, 1351–1361.

The invention claimed is:

1. A method of treating pathologies associated with GSK-3β and casein kinase 1 selected from the group consisting of lung cancer, breast cancer, prostate cancer and colon cancer, said method comprising administering to a patient in need thereof a therapeutically efficient amount of a compound of formula I

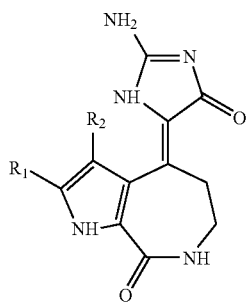

(1)

in which R1 and R2, identical or different, represent H or Br, or a pharmaceutically acceptable salt thereof, such that said at least one of GSK-3β and casein kinase 1 is inhibited.

2. The method according to claim 1, wherein the compound is 4-(2-amino-4-oxo-2-imidazolin-5-ylidene)-4,5,6,7-tetrahydropyrrolo (2,3-c) azepine-8-one, or a pharmaceutically acceptable salt thereof.

3. The method according to claim 1, wherein the compound is 4-(2-amino-4-oxo-2-imidazolin-5-ylidene)-2-bromo-4,5,6,7-tetrahydropyrrolo (2,3-c) azepine-8-one, or a pharmaceutically acceptable salt thereof.

4. The method according to claim 1, wherein said compound is administered to said patient by an oral route.

5. The method according to claim 1, wherein said compound is administered to said patient by an injectable route.

6. The method of claim 1 wherein said patient is a dog or a person.

7. The method of claim 1 wherein said salt is an acid addition salt.

8. The method of claim 7 wherein said acid is selected from the group consisting of acetic acid, ascorbic acid, maleic acid, phosphoric acid, salicylic acid and tartric acid.

* * * * *